(12) United States Patent
Dowling et al.

(10) Patent No.: US 7,674,791 B2
(45) Date of Patent: Mar. 9, 2010

(54) TRIAZOLOPYRAZINES AND METHODS OF MAKING AND USING THE SAME

(75) Inventors: James E. Dowling, Scituate, MA (US); Gang Yao, Sudbury, MA (US); Hexi Chang, Belmont, MA (US); Hairuo Peng, Chestnut Hill, MA (US); Jeffrey Vessels, Marlborough, MA (US); Russell C. Petter, Stow, MA (US); Gnanasambandam Kumaravel, Westford, MA (US)

(73) Assignee: Biogen IDEC MA Inc., Cambridge, MA (US)

( * ) Notice: Subject to any disclaimer, the term of this patent is extended or adjusted under 35 U.S.C. 154(b) by 642 days.

(21) Appl. No.: 10/552,305

(22) PCT Filed: Apr. 9, 2004

(86) PCT No.: PCT/US2004/011006

§ 371 (c)(1),
(2), (4) Date: Aug. 29, 2006

(87) PCT Pub. No.: WO2004/092177

PCT Pub. Date: Feb. 28, 2004

(65) Prior Publication Data

US 2007/0010520 A1    Jan. 11, 2007

Related U.S. Application Data

(60) Provisional application No. 60/461,546, filed on Apr. 9, 2003.

(51) Int. Cl.
    *A61K 31/4985* (2006.01)
(52) U.S. Cl. ...................... 514/249; 544/350
(58) Field of Classification Search ............... 544/350
    See application file for complete search history.

(56) References Cited

U.S. PATENT DOCUMENTS

| | | | |
|---|---|---|---|
| 4,739,053 | A | 4/1988 | Albert et al. |
| 5,204,353 | A | 4/1993 | Meier |
| 5,356,894 | A | 10/1994 | Rodney et al. |
| 5,458,135 | A | 10/1995 | Patton et al. |
| 5,747,496 | A | 5/1998 | Cox et al. |
| 6,005,109 | A | 12/1999 | Faraci et al. |
| 6,107,301 | A | 8/2000 | Aldrich et al. |
| 6,197,788 | B1 | 3/2001 | Fletcher et al. |
| 6,583,156 | B1 | 6/2003 | Gillespie et al. |
| 6,608,085 | B1 | 8/2003 | Gillespie et al. |
| 6,787,541 | B1 | 9/2004 | Gillespie et al. |

FOREIGN PATENT DOCUMENTS

| | | |
|---|---|---|
| EP | 0390112 | 10/1990 |
| EP | 0459702 | 12/1991 |
| EP | 0496617 | 7/1992 |
| EP | 0515107 | 11/1992 |
| EP | 0666079 | 8/1995 |
| EP | 0667349 | 8/1995 |
| EP | 0976753 | 2/2000 |
| EP | 0976755 | 2/2000 |
| EP | 0992510 | 4/2000 |
| EP | 1221444 | 1/2001 |
| EP | 1116722 | 7/2001 |
| EP | 1300147 | 4/2003 |
| FR | 223066 | 5/1974 |
| JP | 56131586 | 10/1981 |
| JP | 56131587 | 10/1981 |
| JP | 59062595 | 4/1984 |
| JP | 60140335 | 7/1985 |
| JP | 04036284 | 2/1992 |
| WO | WO9320078 | 10/1993 |
| WO | WO9413643 | 6/1994 |
| WO | WO9413677 | 6/1994 |
| WO | WO9417803 | 8/1994 |
| WO | WO9713676 | 4/1997 |
| WO | WO9901439 | 1/1999 |
| WO | WO9901454 | 1/1999 |
| WO | WO9943678 | 2/1999 |
| WO | WO9921617 | 5/1999 |
| WO | WO9940091 | 8/1999 |
| WO | WO9948903 | 9/1999 |
| WO | WO9962518 | 12/1999 |
| WO | WO0017201 | 3/2000 |
| WO | WO0061586 | 10/2000 |
| WO | WO0102400 | 1/2001 |

(Continued)

OTHER PUBLICATIONS

Koretskaya et al., Khim.-Farm. Zh. I (1968) 2(6) 5-12.

(Continued)

*Primary Examiner*—James O Wilson
*Assistant Examiner*—Brian McDowell
(74) *Attorney, Agent, or Firm*—Lando & Anastasi, LLP

(57) ABSTRACT

The invention is based on the discovery that compounds of formula (I) possess unexpectedly high affinity for the A2a adenosine receptor, and can be useful as antagonists thereof for preventing and/or treating numerous diseases, including Parkinson's disease. In one embodiment, the invention features a compound of formula I (See formula on paper copy)

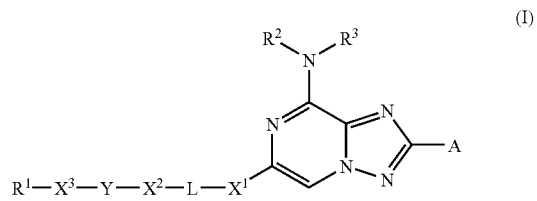

13 Claims, No Drawings

FOREIGN PATENT DOCUMENTS

| | | |
|---|---|---|
| WO | WO0102409 | 1/2001 |
| WO | WO0162233 | 8/2001 |
| WO | WO03020723 | 3/2003 |
| WO | WO03048163 | 6/2003 |
| WO | WO03068776 | 8/2003 |
| WO | WO2004029056 | 4/2004 |

OTHER PUBLICATIONS

Mamaev et al., Getertsikl, Soedin, (1971) 7, 535.
Pendergast et al., J. Chem. Soc. Perkin. Trans. (1973) 1, 2759-2763.
Machon et al., J. Pharmacol. Pharm. (1976) 28, 511.
Higashino et al., Chem Pharm Bull 24, 238-52 (1976).
Higashino et al., Chem Pharm Bull 24, 3120-34 (1976).
Hayashi et al., Yakugaku Zasshi 98, 891 (1978) Abstract.
Robev et al., Dokl. Bolg. Akad. Nauk. (1978) 31, 1131-1134.
Higashino et al., Chem. Pharm. Bull. (1979) 27, 2431.
Higashino et al., Chem. Pharm. Bull. (1979) 27, 3176.
Higashino et al., Fukusokan Kagaku Toronkai Koen Yoshishu, 12th, 1979, 171-5 (Japanese language Conference Report).
Press et al., J. Org. Chem. 48, 4605 (1983).
Schechter et al (1985) J Clin Pharmacol 25, 276.
Higashino et al., Chem Pharm Bull 33, 950 (1985).
Bruns et al., (1986) Mol. Pharmacol. 29: 331-346.
Higashino et al., Chem Pharm Bull 34, 4352 (1986).
Higashino et al., Chem Pharm Bull 34, 4569 (1986).
Molina et al., Tetrahedron Letters (1987) 28, 4451-4454.
Higashino et al., Chem Pharm Bull 35, 4078 (1987).
Jaskolski et al., Acta Crystallogr Sect. C, (1987) C43, 2110-2113.
Molina et al., J. Org. Chem., (1988) 53, 4653-63.
Miyashita et al., Chem Pharm Bull 38, 230(1990).
Hamamichi et al., J. Heterocycl. Chem (1990) 31, 321.
Hamamichi et al., J. Heterocycl. Chem (1990) 27, 835.
Skalski et al., Can. J. Chem (1990) 68, 2164-2170.
Jacobsen et al., J. Med. Chem. (1992) 35(3), 407-423.
Chemical Abstracts, V. 118, No. 3 (1993) Abstract # 22077 Suzuki, Hitomi et al (J. Org. Chem (1993) 58(1) 241-4).
Chemical Abstracts, V. 121, No. 9 (1994) Abstract # 108677 Bouillon et al (Heterocycles (1994) 37(2) 915-32).
Gunderson, Tetrahedron Lett (1994) 35, 3155.
Colotta et al., Eur. J. Jed. Chem. (1995) 30(2), 133-139.
Gundersen et al., Tetrahedron Letters (1995) 36(11), 1945-1948.
Stevenson et al., Tetrahedron Lett. (1996) 37, 8375-8378.
Langli et al., Tetrahedron, vol. 52, Issue 15, Apr. 8, 1996, pp. 5625-5638.
Bertorelli et al (1996) Drug Development Research 37, Issue 2, pp. 65-72.
Prassad et al., Tetrahedron (1997) 53, 7237-7254.
Chebib et al., Bioorganic & Med. Chem Lett (1997) 5(2) 311-322.
Biraldi et al., J. Med. Chem. (1998) 41, 2126-2133.
Francis et al., J. Med. Chem. (1998) 31, 1014-1020.
Monopoli et al. (1998) J Pharmacol Exp Ther 285 (1): 9.
Kim et al., Arch. Pharmacal. Res. (1998) 21, 458-464.
Molina et al., J. Org. Chem. (1998) 53, 4653-4663.
Suzuki et al., Chem Pharm Bull 46, 199 (1998).
Monopoli et al (1998) NeuroReport 9, 3955-3959.
Strappaghetti et al, Eur. J. Med. Chem (1998) 33, 501-508.
Chorvat et al., J. Med. Chem. (1999) 42(5), 833-848.
Betti et al., *Eur. J. Med Chem* (1999) 34(10) 867-875.
Cocuzza et al., Bioorganic & Med. Chem Lett (1999) 9(7) 1063-1066.
Fredholm et al., (1999) Pharmacol Rev. 51, 83-133.
Kopf et al. (1999) Psychopharmacol., 146, 214-219.
Li et al (1999) Experimental Eye Research 68, 9-17.
Svenningsson et al (1999) Progress in Neurobiology 59, 355-396.
Alarcon et al, Tetrahedron Lett (2000) 41, 7211-7215.
Alarcon et al, Bioorg Med Chem Lett (2001) 11, 1855-1858.
Stone et al., (2001) Drug Development Research 52, 323.
Scammell et al., (2001) Neuroscience 107, 653.
ElYacoubi et al., (2001) British Journal of Pharmacology 134, 68-77.
Kase (2001) Bioscience, Biotechnology, and Biochemistry 65, 1447-1457.
Behan et al., (2002) British Journal of Pharmacology (2002) 135, 1435-1442.
Ikeda et al (2002) J Neurochem. 80, 262-70.
Bastia et al., (2002) Neuroscience Letters 328, 241-244.
Hauser et al (2003) Neurology 61 297.
Urade et al (2003) Neurology 2003;61:S94-S96.
Varani et al. (2003) FASEB J. 17, 2148-2150.
Dall'lgna et al., (2003) Br J Pharmacol 138: 1207-1209.
Chase et al., (2003) Neurology 2003;61:S107-S111.
Bara-Jimenez et al., Neurology 2003 61: 293-296.
Bailey et al. J. Neurosci. 22 (21): 9210-9220.

TRIAZOLOPYRAZINES AND METHODS OF MAKING AND USING THE SAME

CROSS-REFERENCE TO RELATED APPLICATIONS

The present application is a national phase application of International Application No. PCT/US2004/011006, which claims the benefit of U.S. Provisional Application No. 60/461,546, filed Apr. 9, 2003, the contents of each of which are incorporated herein by reference.

BACKGROUND OF THE INVENTION

Adenosine is a ubiquitous biochemical messenger. Adenosine binds to and activates certain seven transmembrane-spanning G-protein coupled receptors, eliciting a variety of physiological responses. Adenosine receptors are divided into four known subtypes (i.e. $A_1$, $A_{2a}$, $A_{2b}$, and $A_3$). These receptor subtypes mediate different and sometimes opposing effects. In general, activation of the adenosine $A_{2a}$ or $A_{2b}$ receptor leads to an increase in cellular cAMP levels, while activation of the adenosine $A_1$ or $A_3$ receptor leads to a decrease in cellular cAMP levels. $A_{2a}$ adenosine receptors are abundant in the basal ganglia, a region of the brain associated with the pathphysiology of Parkinson's disease. For reviews concerning $A_{2a}$ adenosine receptors, see, e.g., Moreau et al., Brain Research Reviews 31:65-82 (1999) and Svenningsson et al., Progress in Neurobiology 59:355-396 (1999). For a discussion of the role and regulation of adenosine in the central nervous system, see, e.g., Dunwiddie et al., Ann. Rev. Neuroscience 24:31-55 (2001).

SUMMARY OF THE INVENTION

The invention is based on the discovery that compounds of formula (I) are unexpectedly potent antagonists of the $A_{2a}$ subtype of adenosine receptors. Many compounds of formula (I) also selectively inhibit the $A_{2a}$ adenosine receptors. Adenosine antagonists of the present invention are useful in the prevention and/or treatment of various diseases and disorders related to modulation of $A_{2a}$ adenosine receptor signaling pathways. Such a disease or disorder can be, e.g., neurodegenerative diseases such as Parkinson's disease and Parkinson's-like syndromes such as progressive supranuclear palsy and multiple system atrophy, senile dementia such as Alzheimer's disease, depression, AIDS encephalopathy, multiple sclerosis, amyotrophic lateral sclerosis, migraine, attention deficit disorder, narcolepsy, sleep apnea or other disorders that cause excessive daytime sleepiness, Huntington's disease, cerebral ischemia, brain trauma, hepatic fibrosis, cirrhosis, and fatty liver.

In one aspect, the invention features compounds of formula (I):

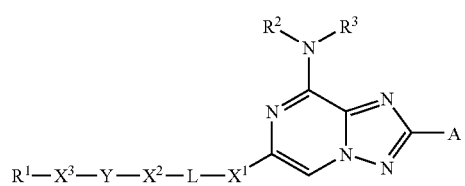

A can be aryl or heteroaryl. Each of $R^2$ and $R^3$, independently, can be hydrogen, alkyl, cycloalkyl, cycloalkenyl, aryl, aralkyl, heterocycloalkyl, heterocycloalkenyl, heteroaryl, or heteroaralkyl. Each of $X^1$, $X^2$, and $X^3$, independently, can be a bond, $C_{1-6}$ alkylene, $C_{2-6}$ alkenylene, or $C_{2-6}$ alkynylene; and each of the just-mentioned $C_{1-6}$ alkylene, $C_{2-6}$ alkenylene, and $C_{2-6}$ alkynylene is either unsubstituted or substituted with alkyl, alkenyl, alkynyl, alkoxy, acyl, halo, hydroxy, amino, nitro, cyano, guanadino, amidino, carboxy, sulfo, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, cycloalkylalkyl, heterocycloalkyl, heterocycloalkyloxy, heterocycloalkylsulfanyl, heterocyloalkylalkyl, aryl, aryloxy, arylsulfanyl, aroyl, aralkyl, heteroaryl, heteroaryloxy, heteroarylsulfanyl, heteroaroyl, or heteroaralkyl. Y can be $-NR^a-$, $-O-$, $-S-$, $-SO-$, $-SO_2-$, $-CO-$, $-CO_2-$, $-O-CO-$, $-CO-NR^a-$, $-NR^a-CO-$, $-SO_2-NR^a-$, $-NR^a-SO_2-$, $-NR^a-CO-NR^b-$, $NR^a-CO-O-$, $-O-CO-NR^a-$, or a bond; where each of $R^a$ and $R^b$, independently, can be hydrogen, alkyl, alkenyl, alkynyl, cycloalkyl, heterocycloalkyl, cycloalkylalkyl, heterocycloalkylalkyl, cycloalkenyl, heterocycloalkenyl, cycloalkenylalkyl, heterocycloalkenylalkyl, aryl, heteroaryl, aralkyl, or heteroaralkyl. $R^1$ is hydrogen, alkyl, alkenyl, alkynyl, cycloalkyl, cycloalkenyl, aryl, or heterocyclyl; each of said alkyl, alkenyl, alkynyl, cycloalkyl, cycloalkenyl, aryl, and heterocyclyl being optionally substituted alkyl, alkenyl, alkynyl, alkoxy, formic, acyl, halo, hydroxy, amino, nitro, cyano, guanadino, amidino, oxo, carboxy, sulfo, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, cycloalkylalkyl, heterocycloalkyl, heterocycloalkyloxy, heterocycloalkylsulfanyl, heterocyloalkylalkyl, aryl, aryloxy, arylsulfanyl, aroyl, aralkyl, heteroaryl, heteroaryloxy, heteroarylsulfanyl, heteroaroyl, or heteroaralkyl. L is a bond or a linker selected from the group consisting of:

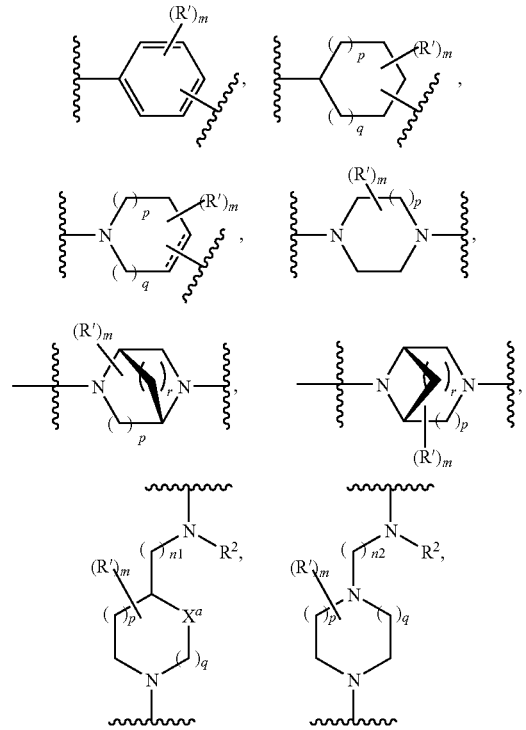

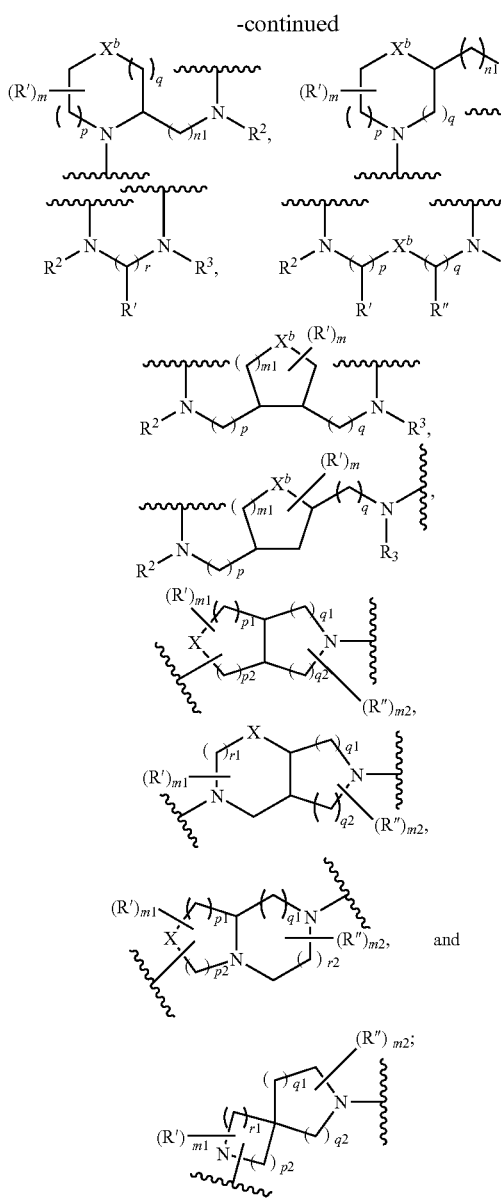

wherein each of R' and R", independently, can be hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl (note that two adjacent R' groups can join together to form a 4- to 8-membered optionally substituted cyclic moiety); $X^a$ can be —C($R^2$)($R^3$)—, —S—, —SO—, or —$SO_2$—; $X^b$ is —C($R^2$)($R^3$)—, —$NR^2$—, —O—, —S—, —SO—, or —$SO_2$—; each of p, q, and m, independently, can be 0-3; each of m1 and m2, independently, can be 0-2; each of r and r1, independently, can be 1 or 2; each of p1, p2, q1, and q2, independently, can be 0-2; r2 can be 0 or 1; n1 can be 0-6; and n2 can be 2-6.

In one embodiment, $X^1$ can be alkynylene. In one embodiment, L can be a bond or a linker selected from the group consisting of:

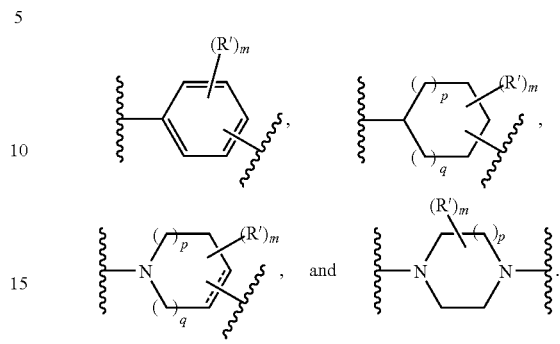

In one embodiment, each of $X^2$ and $X^3$, independently, can be a bond or alkylene. In one embodiment, Y can be —$NR^a$—, —O—, —S—, —CO—O—, —O—CO—, —CO—$NR^a$—, —$NR^a$—CO—, or a bond. In one embodiment, $R^1$ can be alkyl, cycloalkyl, heterocycloalkyl, aryl, or heteroaryl.

In one embodiment, $X^1$ is alkynylene (e.g., $C_{2-4}$ alkylene such as propynyl); L is a bond; each of $X^2$ and $X^3$ is indepedently a bond or alkylene (e.g., $C_{1-4}$ alkynylene); Y is a bond or —$NR^a$— where $R^a$ is hydrogen or alkyl (e.g., $C_{1-4}$ alkyl); and $R^1$ is alkyl (e.g., $C_{1-4}$ alkyl), cycloalkyl (e.g., $C_{4-6}$ cycloalkyl), heterocycloalkyl (e.g., 5- to 6-membered N-containing heterocycloalkyl such as pyrrolidine), aryl (e.g., phenyl or naphthalene), or heteroaryl (e.g., 5- to 6-membered N-containing heteroaryl such as pyridine, furan, or isoxazole, or fused ring-containing heteroaryl such as quinoline or isoquinoline); each of the $R^1$ groups is unsubstituted or substituted with halo, hydroxy, alkyl, aralkyl, or heteroalkyl; A is furls, thienyl, or pyridyl; and each of $R^2$ and $R^3$ is indepedently a bond or $C_{1-4}$ alkyl.

In one embodiment, $X^1$ can be a bond or alkylene. In one embodiment, L can be a bond or

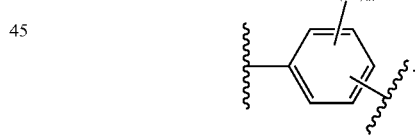

In one embodiment, each of $X^2$ and $X^3$, indepedently, can be a bond, $C_{1-6}$ alkylene, or $C_{2-6}$ alkenylene. In one embodiment, Y can be a bond, —CO—, —CO—O—, —O—CO—, —CO—$NR^a$—, or —$NR^a$—CO—. In one embodiment, $R^1$ can be hydrogen, or $R^1$ can be alkyl (e.g., $C_{1-4}$ alkyl), cycloalkyl (e.g., $C_{4-6}$ cycloalkyl), heterocycloalkyl (e.g., 5- to 6-membered N-containing heterocycloalkyl such as pyrrolidine), aryl (e.g., phenyl or naphthalene), or heteroaryl (e.g., 5- to 6-membered N-containing heteroaryl such as pyridine, furan, or isoxazole, or fused ring-containing heteroaryl such as quinoline or isoquinoline); each of the alkyl, cycloalkyl, heterocycloalkyl, aryl, or heteroaryl can be unsubstituted or substituted with alkyl, halo, hydroxy, alkoxycarbonyl, aminocarbonyl, aryl, aralkyl, heteroaryl, or heteroaralkyl.

In one embodiment, each of $X^1$ and $X^2$, indepedently, can be a bond; L can be a bond or

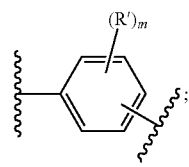

Y can be —CO—, —CO—O—, —O—CO—, —CO—NR$^a$—, or —NR$^a$—CO— where R$^a$ can be hydrogen or alkyl; X$^3$ can be C$_{1-6}$ alkylene; R$^1$ can be hydrogen, or R$^1$ can be alkyl, cycloalkyl, heterocycloalkyl, aryl, or heteroaryl, and each of the alkyl, cycloalkyl, heterocycloalkyl, aryl, or heteroaryl is unsubstituted or substituted with alkyl, halo, hydroxy, alkoxycarbonyl, aminocarbonyl, aryl, aralkyl, heteroaryl, or heteroaralkyl; A can be furyl, thienyl, or pyridyl; and each of R$^2$ and R$^3$, indepedently, can be a bond or C$_{1-4}$ alkyl.

In one embodiment, X$^1$ can be a bond; L can be a bond or

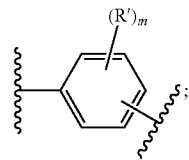

X$^2$ can be a bond, C$_{1-6}$ alkylene, or C$_{2-6}$ alkenylene; Y can be a bond, —CO—, —O—, —CO—NR$^a$—, or —NR$^a$—CO— where R$^a$ can be hydrogen or alkyl; X$^3$ can be a bond or C$_{1-6}$ alkylene; R$^1$ can be aryl or heterocycloalkyl, each of the aryl or heteroaryl can be unsubstituted or substituted with alkyl, halo, alkylsulfanyl, or amino; A can be furyl, thienyl, or pyridyl; and each of R$^2$ and R$^3$, independently, can be a bond or C$_{1-4}$ alkyl.

In one embodiment, L can be

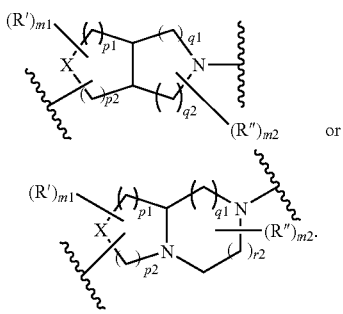

For example, L can be

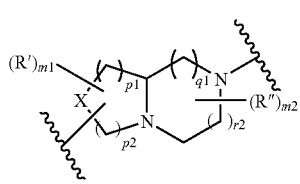

wherein X is —CH$_2$—, p1 is 1, p2 is 1 or 2, q1 is 1, r2 is 1 or 2, each of m1 and m2 is independently 0 or 1, and each of R' and R" is independently hydrogen or alkyl. In one embodiment, R$^1$ is cycloalkyl, cycloalkylalkyl, aryl, aralkyl, heterocyclyl, or heterocyclylalkyl.

In another aspect, the invention features a compound of the following formula:

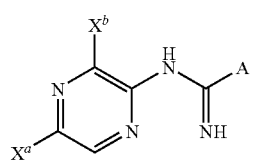

(III)

A can be aryl (e.g., phenyl) or heteroaryl (e.g., pyrazine, furan, thiophene, indole, thiazole, or pyrrole); and each of X$^a$ and X$^b$, independently, can be chloro, bromo, or iodo (e.g., both X$^a$ and X$^b$ can be bromo). Examples of a compound of formula (III) are N-(3,5-dibromo-pyrazin-2-yl)-furan-2-carboxamidine are N-(3,5-durum-pyrazin-2-yl)-thiophene-2-carboxamidine.

In another aspect, the invention features a compound of the following formula:

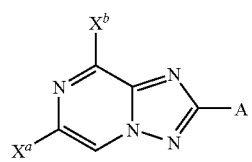

(IV)

A can be aryl (e.g., phenyl) or heteroaryl (e.g., pyrazine, furan, thiophene, indole, thiazole, or pyrrole); and each of X$^a$ and X$^b$, independently, can be chloro, bromo, or iodo (e.g., both X$^a$ and X$^b$ can be bromo). Examples of a compound of formula (III) are 6,8-dibromo-2-furan-2-yl-[1,2,4]triazolo[1,5-a]pyrazine are 6,8-dibromo-2-thiophen-2-yl-[1,2,4]triazolo[1,5-a]pyrazine.

In another aspect, the invention features a compound of the following formula:

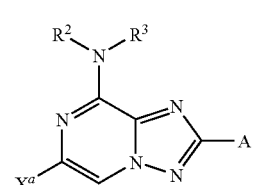

(V)

A can be aryl (e.g., phenyl) or heteroaryl (e.g., pyrazine, furan, thiophene, indole, thiazole, or pyrrole); and each of R$^2$ and R$^3$, independently, can be hydrogen, alkyl, cycloalkyl, cycloalkenyl, aryl, aralkyl, heterocycloalkyl, heterocycloalkenyl, heteroaryl, or heteroaralkyl (e.g., each of R$^2$ and R$^3$ is independently hydrogen or alkyl); and X$^a$ can be chloro, bromo, or iodo (e.g., bromo). Some examples of a compound of formula (V) are 6-bromo-2-furan-2-yl-[1,2,4]triazolo[1,5-a]pyrazin-8-ylamine, 6-bromo-2-thiophen-2-yl-[1,2,4]triazolo[1,5-a]pyrazin-8-ylamine, 2-furan-2-yl-6-iodo-[1,2,4]

triazolo[1,5-a]pyrazin-8-ylamine, and 6-iodo-2-thiophen-2-yl-[1,2,4]triazolo[1,5-a]pyrazin-8-ylamine.

In another aspect, the invention includes a method of preparing a compound of the following formula:

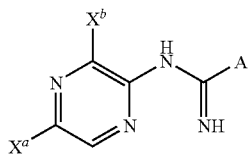

(III)

A can be aryl or heteroaryl; and each of $X^a$ and $X^b$ is independently chloro, bromo, or iodo. The method includes reacting a pyrazine of formula (II)

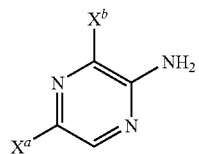

(II)

with a cyano-substited compound A (where $X^a$, $X^b$, and A have been defined above) in the presence of a Lewis acid to form a compound of formula (III). For example, A can be phenyl, pyrazine, furan, thiophene, indole, thiazole, or pyrrole; and both $X^a$ and $X^b$ can be bromo. Examples of the Lewis acid are $AlCl_3$ and $ZnCl_2$.

The invention also features a method of preparing a compound of the following formula:

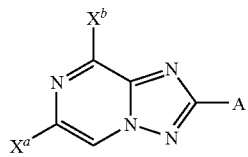

(IV)

A can be aryl (e.g., phenyl) or heteroaryl (e.g., pyrazine, furan, thiophene, indole, thiazole, or pyrrole); and each of $X^a$ and $X^b$, independently, can be chloro, bromo, or iodo (e.g., both $X^a$ and $X^b$ can be bromo). The method includes cyclizing a compound of formula (III), which has been defined above, in the presence of an oxidizing agent (e.g., $Pb(OAc)_4$, NaOCl, or 2-iodoxybenzoic acid) to form a compound of formula (IV).

The invention also features a method of preparing a compound of the following formula:

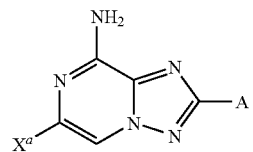

(V)

A can be aryl (e.g., phenyl) or heteroaryl (e.g., pyrazine, furan, thiophene, indole, thiazole, or pyrrole), and $X^a$ can be chloro, bromo, or iodo (e.g., bromo). The method comprising aminating a compound of formula (IV), which has been defined above, in the presence of anhydrous ammonia, to form a compound of formula (V).

Preparation of a compound of formula (V) from a compound of formula (II) using the methods described above is also within the scope of this invention.

Some examples of a compound of formula (I) are shown in Examples 1-230 below.

An N-oxide derivative or a pharmaceutically acceptable salt of each of the compounds of formula (I), formula (III), formula (IV), and formula (V) is also within the scope of this invention. For example, a nitrogen ring atom of the triazolotriazine or the pyrazolotriazine core ring or a nitrogen-containing heterocyclyl substituent can form an oxide in the presence of a suitable oxidizing agent such as m-chloroperbenzoic acid or $H_2O_2$.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such an acid include hydrochloric acid, hydrobromic acid, hydroiodic acid, sulfuric acid, methanesulfonic acid, phosphoric acid, p-bromophenyl-sulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to a skilled person in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Compounds of formula (I) can also be, e.g., in a form of achiral compounds, racemic mixtures, optically active compounds, pure diastereomers, or a mixture of diastereomers.

Compounds of formula (I) exhibit surprisingly high affinity to the $A_{2a}$ subtype of adenosine receptors, e.g., with $K_i$ values of less than 10 µM under conditions as described in Example 231. Some compounds of formula (I) exhibit $K_i$ values of below 1 µM. Many compounds of formula (I) are selective inhibitors of the $A_{2a}$ adenosine receptors (e.g., these compounds inhibit the $A_{2a}$ adenosine receptors at least 10 times better than the other subtypes of adenosine receptors, e.g., the $A_1$ adenosine receptors or the $A_3$ adenosine receptors).

Compounds of formula (I) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

In another aspect, the present invention features a pharmaceutical composition comprising a compound of formula (I) (or a combination of two or more compounds of formula (I)) and a pharmaceutically acceptable carrier. Also included in the present invention is a medicament composition including any of the compounds of formula (I), alone or in a combination, together with a suitable excipient.

In a further aspect, the invention features a method of inhibiting the $A_{2a}$ adenosine receptors (e.g., with an $K_i$ value of less than 10 μM; preferably, less than 1 μM) in a cell, including the step of contacting the cell with an effective amount of one or more compounds of formula (I). Also with the scope of the invention is a method of modulating the $A_{2a}$ adenosine receptor signaling pathways in a cell or in a subject (e.g., a mammal such as human), including the step of contacting the cell with or administering to the subject an effective amount of one or more of a compound of formula (I).

Also within the scope of the present invention is a method of treating a subject or preventing a subject suffering from a condition or a disease wherein the causes or symptoms of the condition or disease are associated with an activation of the $A_{2a}$ adenosine receptor. The method includes the step of administering to the subject an effective amount of one or more of a compound of formula (I). The conditions or diseases can be, e.g., neurodegenerative diseases such as Parkinson's disease and Parkinson's-like syndromes such as progressive supranuclear palsy and multiple system atrophy, senile dementia such as Alzheimer's disease, depression, AIDS encephalopathy, multiple sclerosis, amyotrophic lateral sclerosis, migraine, attention deficit disorder, narcolepsy, sleep apnea or other disorders that cause excessive daytime sleepiness, Huntington's disease, cerebral ischemia, brain trauma, hepatic fibrosis, cirrhosis, and fatty liver.

Compounds of formula (I) may be utilized as sedatives, muscle relaxants, antipsychotics, antidepressants, anxiolytics, analgesics, respiratory stimulants, antiepileptics, anticonvulsants, and cardioprotective agents.

Also within the scope of the invention is a method of treating or preventing a condition or a disease characterized by or resulted from an over-activation of the $A_{2a}$ adenosine receptor by administering to a subject in need of such a treatment an effective amount of any of compounds of formula (I) in combination with one or more known $A_{2a}$ antagonists. For example, a patient suffering from Parkinson's disease can be treated by administering an effective amount of a compound of formula (I) in combination with an agent such as L-DOPA, a dopaminergic agonist, an inhibitor of monoamine oxidase (type B), a DOPA decarboxylase inhibitor, or a catechol-O-methyltransferase inhibitor. The compound of formula (I) and the agent can be administered to a patient simultaneously or in sequence. The invention also includes a pharmaceutical composition containing one or more of a compound of formula (I), one or more of a known $A_{2a}$ antagoinst, and a suitable excipient.

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkylene" is a divalent alkyl group, as defined herein.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkenylene" is a divalent alkenyl group, as defined herein.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy. An "alkynylene" is a divalent alkynyl group, as defined herein.

As used herein, an "amino" group refers to —NR$^X$R$^Y$ wherein each of R$^X$ and R$^Y$ is independently hydrogen, alkyl, cycloalkyl, (cycloalkyl)alkyl, aryl, aralkyl, heterocycloalkyl, (heterocycloalkyl)alkyl, heteroaryl, or heteroaralkyl. When the term "amino" is not the terminal group (e.g., alkylcarbonylamino), it is represented by —NR$^X$—R$^X$ has the same meaning as defined above.

As used herein, an "aryl" group refers to phenyl, naphthyl, or a benzofused group having 2 to 3 rings. For example, a benzofused group includes phenyl fused with one or two $C_{4-8}$ carbocyclic moieties, e.g., 1,2,3,4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl.

As used herein, a "cycloalkyl" group refers to an aliphatic carbocyclic ring of 3-10 (e.g., 48) carbon atoms. Examples of cycloalkyl groups include cyclopropyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, and bicyclo[3.2.3]nonyl, A "cycloalkenyl" group, as used herein, refers to a non-aromatic carbocyclic ring of 3-10 (e.g., 4-8) carbon atoms having one or more double bond. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]often, and bicyclo[3.3.1]nonenyl. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, a "heterocycloalkyl" group refers to a 3- to 10-membered (e.g., 4- to 8-membered) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.0$^{3,7}$] nonyl. A "heterocycloalkenyl" group, as used herein, refers to a 3- to 10-membered (e.g., 4- to 8-membered) non-aromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

A "heteroaryl" group, as used herein, refers to a monocyclic, bicyclic, or tricyclic ring structure having 5 to 15 ring atoms wherein one or more of the ring atoms is a heteroatom, e.g., N, O, or S and wherein one ore more rings of the bicyclic or tricyclic ring structure is aromatic. Some examples of heteroaryl are pyridyl, furyl, pyrrolyl, thienyl, thiazolyl, oxazolyl, imidazolyl, indolyl, tetrazolyl, benzofuryl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or alkyl-C(=O)— where "alkyl" has been defined previously. Acetyl and pivaloyl are examples of acyl groups.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ is alkyl, cycloalkyl, (cycloalkyl)alkyl, aryl, aralkyl, heterocycloalkyl, (heterocycloalkyl)alkyl, heteroaryl, or heteroaralkyl.

As used herein, a "carboxy" and a "sulfo" group refer to —COOH and —SO$_3$H, respectively.

As used herein, an "alkoxy" group refers to an alkyl-O— group where "alkyl" has been defined previously.

As used herein, a "sulfoxy" group refers to —O—SO—R$^X$ or —SO—O—R$^X$, where R$^X$ has been defined above.

As used herein, a "halogen" or "halo" group refers to fluorine, chlorine, bromine or iodine.

As used herein, a "sulfamoyl" group refers to the structure —SO$_2$—NR$^X$R$^Y$ or —NR$^X$—SO$_2$—R$^Z$ wherein R$^X$, R$^Y$, and R$^Z$ have been defined above.

As used herein, a "sulfamide" group refers to the structure —NR$^X$—S(O)$_2$-NR$^Y$R$^Z$ wherein R$^X$, R$^Y$, and R$^Z$ have been defined above.

As used herein, a "urea" group refers to the structure —NR$^X$—CO—NR$^Y$R$^Z$ and a "thiourea" group refers to the structure —NR$^X$—CS—NR$^Y$R$^Z$R$^X$, R$^Y$, and R$^Z$ have been defined above.

As used herein, an effective amount is defined as the amount which is required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

An antagonist is a molecule that binds to the receptor without activating the receptor. It competes with the endogenous ligand(s) or substrate(s) for binding site(s) on the receptor and, thus inhibits the ability of the receptor to transduce an intracellular signal in response to endogenous ligand binding.

As compounds of formula (I) are antagonists of the $A_{2a}$ subtype of the adenosine receptors, these compounds are useful in inhibiting the consequences of signal transduction through the adenosine $A_{2a}$ receptor. Thus, compounds of formula (I) possess the therapuetical utility of treating and/or preventing disorders or diseases for which inhibition of the adenosine $A_{2a}$ receptor signaling pathways is desirable (e.g., Parkinson's disease or depression).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

Other features and advantages of the invention will be apparent from the following detailed description, and from the claims.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable materials and methods are described below. All publications, patent applications, patents, and other references mentioned herein are incorporated by reference in their entirety. In addition, the materials, methods, and examples are illustrative only and are not intended to be limiting.

Synthesis of the Adenosine Antagonist Compounds

Compounds of formula (I) may be prepared by a number of known methods from commercially available or known starting materials.

In one method, a compound of formula (I) is prepared via a key starting material of formula (V):

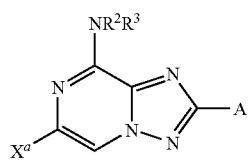

wherein A is aryl or heteroaryl, $R^2$ and $R^3$ are both hydrogen, and $X^a$ is chloro, bromo, or iodo. This compound of formula (V) can be prepared according to the method depicted in Scheme 1 below. Specifically, a compound of formula (II), where each of $X^a$ and $X^b$ is independently chloro, bromo, or iodo, can react with a cyano-substituted compound A, where A has been defined immediately, to form an amidine intermediate of formula (III) in the presence of a Lewis acid, preferably a strong Lewis acid such as $AlCl_3$ or $ZnCl_2$. This reaction can take place in a wide variety of solvents, e.g., toluene, nitrobenzene, or dichloroethane, at an elevated temperature, e.g., in the range of 80° C. to 120° C. Alternatively, the amidine formation reaction can be conducted using potassium t-butoxide in THF at reflux. The amidine intermediate (III) can oxidatively cyclize in the presence of a reagent such as $Pb(OAc)_4$, NaOCl, or 2-iodoxybenzoic acid (IBX) to form a triazolopyrazine of formula (IV), which can then be treated with ammonia to yield a compound of formula (V). See, e.g., Examples 1A-1C below.

As mentioned above, the amidine synthesis can take place in many solvents. Generally, it was found that the efficiency of conversion to the amidine product is directly correlated to the solubility of the starting material in the solvent. Dichloroethane and nitrobenzene are the preferred solvents among the solvents tested. The amidine synthesis was also examined with different amounts of Lewis acid such as $AlCl_3$. It was found that the reaction generally converts with high efficiency (i.e., % conversion) when the amount of Lewis acid ranging from about 0.25 equiv. (relative to the amount of compound (II)) to about 2.5 equiv. (preferably from about 0.5 equivalent to about 2.0 equivalents) was used. The most efficient conversion occurred when about 0.8 to about 1.2 equiv. of Lewis acid was used. For example, one exemplary set of condition employ nitrobenzene or dichloroethane, a reaction temperature of around 110° C., and 1 equiv. of $AlCl_3$.

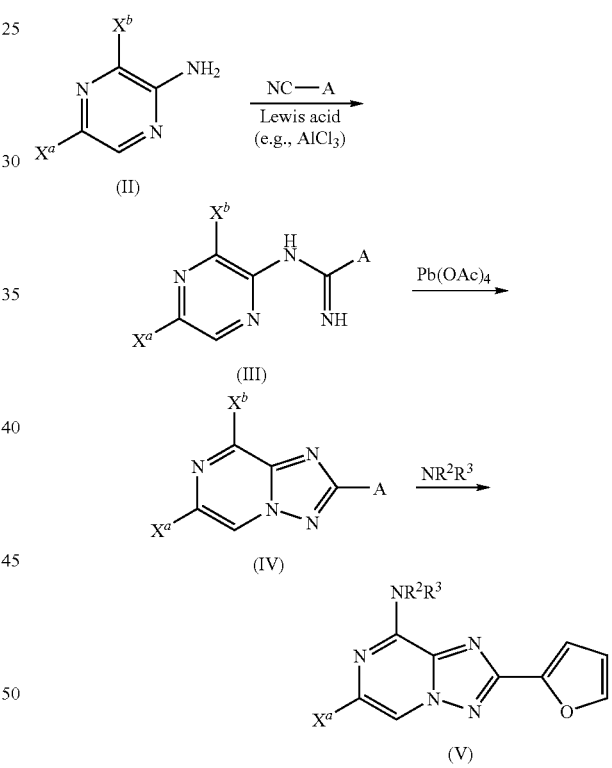

Scheme 1

Alternatively, the key starting material of formula (V) can be prepared according to the method depicted in Scheme 2 below. Specifically, one can use the same compound (II) as described in Scheme 1 above to react with an aminating agent such as t-butyl O-mesitylene carbamate to form a pyrazinium salt intermediate (VI) See Journal of Heterocyclic Chemistry, 12 (1):107-110 (1975) for the preparation of the aminating agent. The pyrazinium salt intermediate (VI) can then undergo a condensation reaction with a compound of the formula A-CHO (i.e., an aryl aldehyde of heteroaryl aldehyde) to form an intermediate of formula (VII), which can react with ammonia to yield a compound of formula (V). See, e.g., Example 2.

Scheme 2

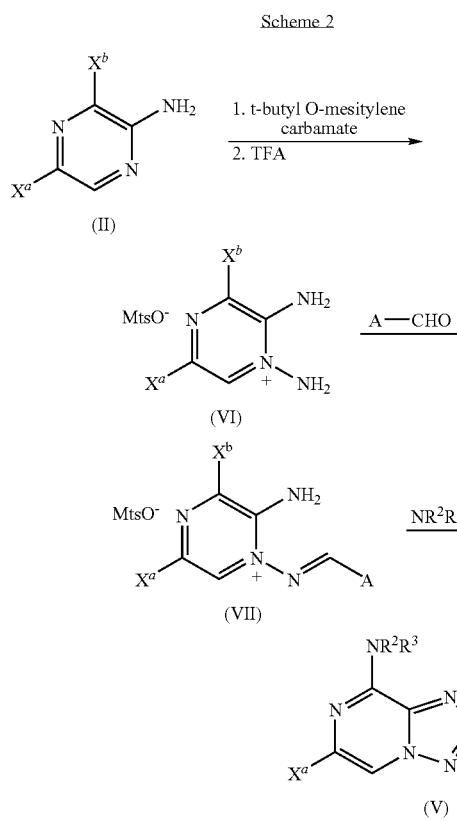

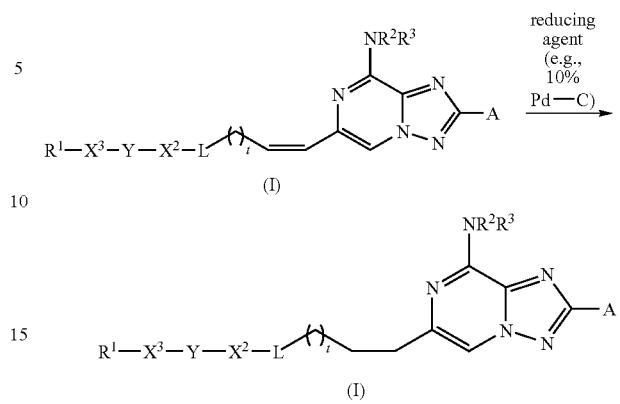

A compound of formula (I) can be prepared from a compound of formula (V) by many known methods. For example, a compound of formula (I) wherein $X^1$, $X^2$, or $X^3$ is directly connected to the triazolopyrazine core ring can be prepared by Sonogashira coupling reaction as shown in Scheme 3 below. Specifically, a compound of formula (V) can react with an optionally substituted alkynyl (e.g., $R^1$—$X^3$—Y—$X^2$-L-$X^{1a}$ wherein $X^{1a}$ is an alkynyl) to form a compound of formula (I) wherein $X^1$ is an alkynylene. See, e.g., Examples 3 and 12 below. Further treatment of this compound of formula (I) with an appropriate reducing agent yields a compound of formula (I) wherein $X^1$ is an alkylene or alkenylene. See, e.g., Examples 13 and 35 below.

Scheme 3

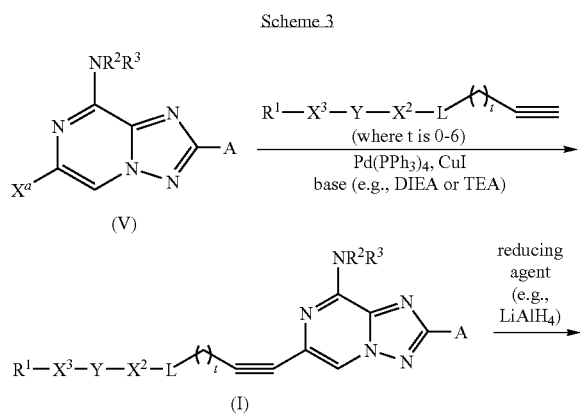

Alternatively, a compound of formula (I) can react with an alkynyl (e.g., a compound of the formula L'-$X^{1a}$ where L' is a precursor of L and $X^{1a}$ has been defined above) to form an intermediate, which can further react with a compound of the formula $R^1$—$X^3$—Y—$X^2$-L" to form a compound of formula (I). As an example, 6-bromo-2-furan-2-yl-[1,2,4]triazolo[1,5-a]pyrazin-8-ylamine can react with prop-2-yn-1-ol to form 3-(8-amino-2-furan-2-yl-[1,2,4]triazolo[1,5-a]pyrazin-6-yl)-prop-2-1-ol, which can then react with phenol in the presence of triphenyl phosphine and diisopropyl azodicarboxylate to form 2-furan-2-yl-6-(3-phenoxy-prop-1-ynyl)-[1,2,4]triazolo[1,5-a]pyrazin-8-ylamine, a compound of formula (I). See, e.g., Example 22 below.

As another example, one can prepare a compound of formula (I) wherein L is a phenyl that connects directly to the triazolopyrazine core ring by using Suzuki coupling reaction as shown in route (A) of Scheme 4 below. Note that $X^a$ is chloro or bromo. See Example 4. On the other hand, if L contains a nitrogen atom that connects directly to the triazolopyrazine core ring (e.g., L is a piperazinyl ring wherein one of the nitrogen ring atoms is connected to the triazolopyrazine core ring), one can react a compound of formula (V) with a compound of the formula $R^1$—$X^3$—Y—$X^2$-L to form a compound of formula (I). See route (B) of Scheme 4 below. As apparent to a skilled person in the art, one can also react a compound L (e.g., a diamine compound such as piperazine or ethylene diamine) with a compound of formula (V) to form an intermediate, which can further react with a compound of the formula $R^1$—$X^3$—Y—$X^2$-LG where LG represents a leaving group (e.g., chloro or bromo) to yield a compound of formula (I). An example of a compound of the formula $R^1$—$X^3$—Y—$X^2$-LG is (3-chloropropyl)benzene.

Scheme 4

(A)

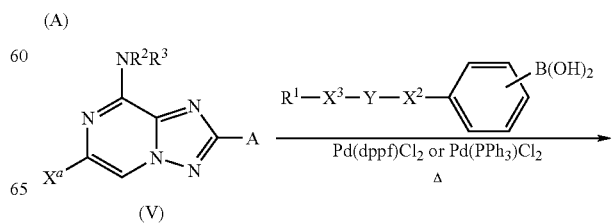

-continued

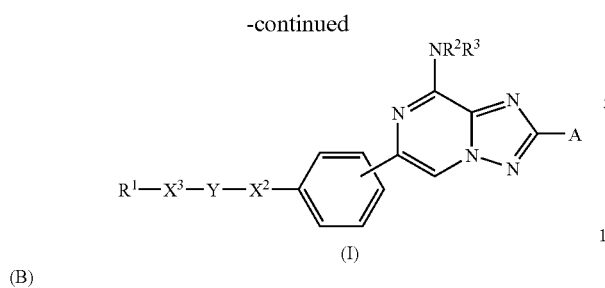

(I)

(B)

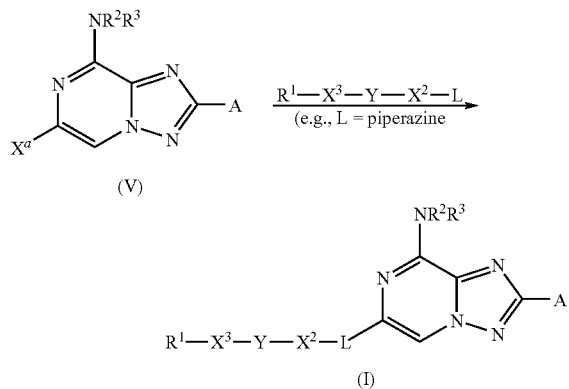

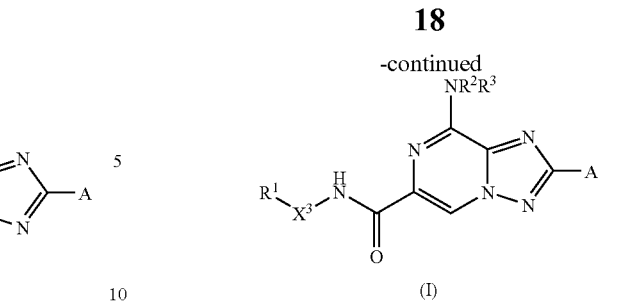

(I)

As a further example, one can prepare a compound of formula (I) wherein Y is —CO—O— that connects directly to the triazolopyrazine core ring as shown in the first reaction of Scheme 5 below. The resulting compound of formula (I) can be converted into other compounds of formula (I) by methods well known to a skilled person in the art. For example, the methyl ester compound of formula (I) can undergo hydrolysis to form a carboxylic acid compound of formula (I), which can further react with an amine to form an amide compound of formula (I). See the second and third reactions of Scheme 5 and Examples 8 and 11 below.

Scheme 5

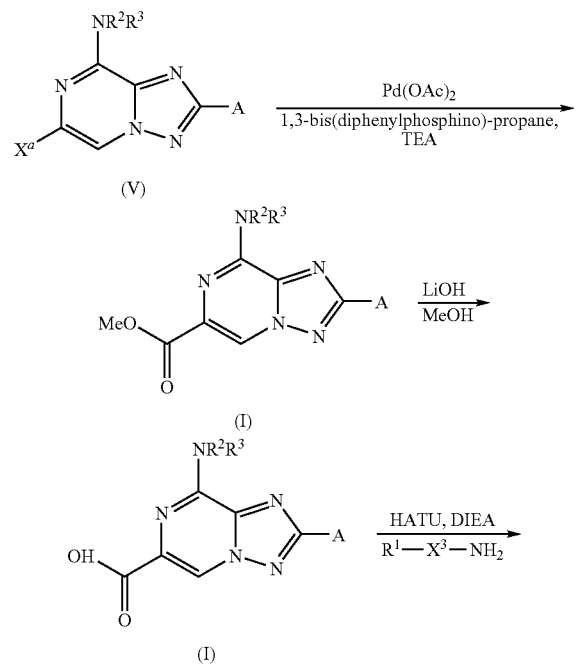

As can be appreciated by the skilled artisan, the above synthetic schemes are exemplary and not intended to comprise a comprehensive list of all means by which the compounds described and claimed in this application may be synthesized. For example, the reaction steps shown in the schemes above can be conducted in a different order. Further methods will be evident to those of ordinary skill in the art.

Uses for the $A_{2a}$ Adenosine Antagonist Compounds

Compounds of the invention are useful in the prevention and/or treatment of various neurological diseases and disorders whose causes or symptoms are associated with the $A_{2a}$ adenosine receptor signaling pathways. Such diseases and disorders include neurodegenerative diseases such as Parkinson's disease and Parkinson's-like syndromes such as progressive supranuclear palsy and multiple system atrophy, Huntington's disease, depression, anxiety, and cerebrovascular disorders such as migraine. In addition, compositions of the invention are useful for neuroprotection, i.e., to prevent or inhibit neuronal death or degeneration associated with conditions such as senile dementia (e.g., Alzheimer's disease), stroke (cerebral ischemia), and brain trauma.

Administration of Compounds of the Invention

Compounds of the invention can be administered to an animal, preferably a mammal, e.g., a human, non-human primate, dog, pig, sheep, goat, cat, mouse, rat, guinea pig, rabbit, hamster, or marmoset. The compounds can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The compounds can be administered orally, intranasally, transdermally, intradermally, vaginally, intraaurally, intraocularly, buccally, rectally, transmucosally, or via inhalation, implantation (e.g., surgically), or intravenous administration.

Optionally, the compounds can be administered in conjunction with a non-adenosine modifying pharmaceutical composition (e.g., in combination with a non-adenosine modifying diuretic as described, for example, in co-pending application PCT/US99/08879 filed Apr. 23, 1999).

Pharmaceutical Compositions

Compounds of the invention can be formulated into pharmaceutical compositions for administration to animals, including humans. These pharmaceutical compositions preferably include a pharmaceutically acceptable carrier and an amount of $A_{2a}$ adenosine receptor antagonist effective to improve neurological functions such as motor functions and cognitive functions.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention can be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention can be aqueous or oleaginous suspension. These suspensions may be formulated according to techniques known in the art using suitable dispersing or wetting agents and suspending agents. The sterile injectable preparation can also be a sterile injectable solution or suspension in a non-toxic parenterally-acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also can contain a long-chain alcohol diluent or dispersant, such as carboxymethyl cellulose or similar dispersing agents which are commonly used in the formulation of pharmaceutically acceptable dosage forms including emulsions and suspensions. Other, commonly used surfactants, such as Tweens, Spans and other emulsifying agents or bioavailability enhancers which are commonly used in the manufacture of pharmaceutically acceptable solid, liquid, or other dosage forms also can be used for the purposes of formulation.

Parenteral formulations can be a single bolus dose, an infusion or a loading bolus dose followed with a maintenance dose. These compositions can be administered once a day or on an "as needed" basis.

The pharmaceutical compositions of this invention be administered orally in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions can be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable earners. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention also can be administered by nasal aerosol or inhalation. Such compositions can be prepared according to techniques known in the art of pharmaceutical formulation, and can be prepared as solutions in saline, employing benzyl alcohol or other suitable preservatives, absorption promoters to enhance bioavailability, fluorocarbons, and/or other conventional solubilizing or dispersing agents.

The amount of $A_{2a}$ adenosine receptor antagonist that may be combined with the carrier materials to produce a single dosage form will vary depending upon the host treated and the particular mode of administration. The compositions can be formulated so that a dosage of between 0.01-100 mg/kg body weight of the $A_{2a}$ adenosine receptor antagonist is administered to a patient receiving these compositions. In some embodiments of the invention, the dosage is 0.1-10 mg/kg body weight. The composition may be administered as a single dose, multiple doses or over an established period of time in an infusion.

A specific dosage and treatment regimen for any particular patient will depend upon a variety of factors, including the particular $A_{2a}$ adenosine receptor antagonist, the patient's age, body weight, general health, sex, and diet, and the time of administration, rate of excretion, drug combination, and the severity of the particular disease being treated. Judgment of such factors by medical caregivers is within ordinary skill in the art. The amount of antagonist will also depend on the individual patient to be treated, the route of administration, the type of formulation, the characteristics of the compound used, the severity of the disease, and the desired effect. The amounts of antagonist can be determined by pharmacological and pharmacokinetic principles well-known in the art.

The invention will be further described in the following examples, which do not limit the scope of the invention described in the claims.

In the following examples, unless indicated otherwise, all commercial reagents were obtained from Sigma-Aldrich (St. Louis, Mo.), Lancaster (Windham N.H.), Acros (Pittsburgh, Pa.), Alfa (Berkshire, UK), TCI (Portland, Oreg.), or Maybridge (Cornwall, UK).

EXAMPLE 1A

6-Bromo-2-furan-2-yl-[1,2,4]triazolo[1,5-a]pyrazin-8-ylamine

Synthesis of the Title Compound is Described in Parts (a)-(c) Below.

(a) N-(3,5-Dibromo-pyrazin-2-yl)-furan-2-carboxamidine

A solution of 3,5-dibromo-pyrazin-2-ylamine (608 mg, 2.4 mmol), furan-2-carbonitrile (297 uL, 3.39 mmol) and AlCl$_3$ (320 mg, 2.4 mmol) in dichloroethane (6 ml) was heated at 115° C. overnight. The reaction was cooled to room temperature and water (5 ml) was added. After 30 minutes, the resulting precipitate was collected and purified by column chromatography (SiO$_2$, THF) to afford 595 mg (72%) of N-(3,5-dibromo-pyrazin-2-yl)-furan-2-carboxamidine as a yellow solid. $^1$H NMR (300 MHz, DMSO-d$_6$) δ 6.73 (dd, J=3.4, 1.8 Hz, 1H), 7.3 (dd, J=3.1 Hz, 1H), 7.98 (s, 1H), 8.49(s, 1H), 8.69 (br. s, 1H).

(b) 6,8-Dibromo-2-furan-2-yl-[1,2,4]triazolo[1,5-a]pyrazine

A mixture of N-(3,5-dibromo-pyrazin-2-yl)-furan-2-carboxamidine (47 g, 0.14 mol), lead tetraacetate (95% purity, 160 g, 0.34 mol), and toluene (940 ml) was refluxed for 2 hours. The reaction was allowed to cool to room temperature and concentrated in vacuo. The resulting residue was purified by flash column chromatography on silica (hexanes:EtOAc (5:1 to 3:1)) as eluent to afford 6,8-dibromo-2-furan-2-yl-[1,2,4]triazolo[1,5-a]pyrazine as a yellow solid (19.2 g, 40% yield). $^1$H NMR (300 MHz, CDCl$_3$) δ 6.60 (dd, 1H), 7.33 (d, 1H), 7.62 (d, 1H), 8.63 (s, 1H).

(c) 6-Bromo-2-furan-2-yl-[1,2,4]triazolo[1,5-a]pyrazin-8-ylamine

Anhydrous ammonia was bubbled over a one-hour period into a solution of 6,8-dibromo-2-furan-2-yl-[1,2,4]triazolo[1,5-a]pyrazine (18.4 g, 0.054 mol) in dioxane (400 ml). The resulting mixture was stirred at room temperature for 2 days during which time the solution was twice recharged with ammonia by bubbling in for one hour. After concentration, diethyl ether (200 ml) was added and the resulted yellow slurry was stirred at room temperature for overnight. 6-Bromo-2-furan-2-yl-[1,2,4]triazolo[1,5-a]pyrazin-8-ylamine was then collected and- dried (15 g, 99% yield). $^1$H NMR (300 MHz, CDCl$_3$) δ 6.70 (dd, 1H), 7.10 (d, 1H), 7.8-8.0 (br m, 3H), 8.58 (s, 1H). MS: m/z: 280 [M+H]$^+$.

EXAMPLE 1B

6-Bromo-2-thiophen-2-yl-[1,2,4]triazolo[1,5-a]pyrazin-8-ylamine

Synthesis of the Title Compound is Described in Parts (a)-(c) Below.

(a) N-(3,5-Dibromo-pyrazin-2-yl)-thiophene-2-carboxamidine

A stirred solution of 3,5-dibromo-pyrazin-2-ylamine (500 mg, 1.98 mmol), thiophene-2-carbonitrile (260 uL, 2.04 mmol) and AlCl$_3$ (232 mg, 1.74 mmol) in dichloroethane (5 ml) was heated at 115° C. overnight. The mixture was allowed to cool to room temperature and diluted with water (5 mL). After 30 minutes, the resulting precipitate was collected and purified by column chromatography (SiO$_2$, THF) to afford 488 mg (68%) of N-(3,5-dibromo-pyrazin-2-yl)-thiophene-2-carboxamidine as a yellow solid. $^1$H NMR (300 MHz, DMSO-d$_6$) δ 7.22 (t, J=3.9 Hz, 1H), 7.83 (dd, J=4.8 Hz, 1H), 7.99 (d, J=4.1 Hz, 1H), 8.49 (s, 1H), 8.88 (br. s, 1H).

(b) 6,8-Dibromo-2-thiophen-2-yl-[1,2,4]triazolo[1,5-a]pyrazine 6,8-Dibromo-2-thiophen-2-yl-[1,2,4]triazolo[1,5-a]pyrazine was prepared in an analogous manner as described in subpart (b) of Example 1A (45% yield). $^1$H NMR (300 MHz, CDCl$_3$) δ 7.17 (d, 1H), 7.50 (d, 1H), 8.00 (dd, 1H), 8.60 (s, 1H).

(c) 6-Bromo-2-thiophen-2-yl-[1,2,4]triazolo[1,5-a]pyrazin-8-ylamine

6-Bromo-2-thiophen-2-yl-[1,2,4]triazolo[1,5-a]pyrazin-8-ylamine was prepared in an analogous manner as described in subpart (c) of Example 1A (88% yield). $^1$H NMR (300 MHz, CDCl$_3$) δ 7.18 (s, 2H), 7.30 (d, 1H), 7.84 (d, 1H), 7.96 (d, 1H), 8.50 (s, 1H). MS: m/z: 296 [M+H]$^+$.

EXAMPLE 1C

6-Bromo-2-(3-fluoro-phenyl)-[1,2,4]triazolo[1,5-a]pyrazin-8-ylamine

Synthesis of the Title Compound is Described in Parts (a)-(c) Below.

(a) N-(3,5-Dibromo-pyrazin-2-yl)-3-fluoro-benzamidine

N-(3,5-Dibromo-pyrazin-2-yl)-3-fluoro-benzamidine was prepared in analogous manner as described in subpart (a) of Example 1A, except that 3-fluoro-benzaldehyde was used instead of furan-2-carbonitrile. N-(3,5-Dibromo-pyrazin-2-yl)-3-fluoro-benzamidine was obtained an off-white solid (3.9 g, 89%). $^1$H NMR (300 MHz, DMSO-d$_6$): δ 6.20 (br s, 1H), 7.20 (br, 1H, partially obscured), 7.45 (dd, 1H), 7.8 (br m, 2H), 8.23 (s, 1H), 9.8. (br s, 1H).

(b) 6,8-Dibromo-2-(3-fluoro-phenyl)-[1,2,4]triazolo[1,5-a]pyrazine 6,8-Dibromo-2-(3-fluoro-phenyl)-[1,2,4]triazolo[1,5-a]pyrazine was prepared in analogous manner as described in subpart (b) of Example 1A (46% yield). $^1$H NMR (300 MHz, CDCl$_3$) δ 7.17 (br s, 1H, partially obscured), 7.47 (dd, 1H), 8.00 (d, 1H), 8.60 (s, 1H), 8.12 (1H, d), 8.65 (s, 1H).

(c) 6-Bromo-2-(3-fluoro-phenyl)-[1,2,4]triazolo[1,5-a]pyrazin-8-ylamine

6-Bromo-2-(3-fluoro-phenyl)-[1,2,4]triazolo[1,5-a]pyrazin-8-ylamine was prepared in analogous manner as described in subpart (c) of Example 1A (74% yield). $^1$H NMR (300 MHz, CDCl$_3$) δ 6.97 (s, 2H), 7.24 (m, 1H), 7.46 (dd, 1H), 7.70 (d, 1H), 7.85 (s, 1H), 8.34 (s, 1H). MS: m/z: 308 [M+H]$^+$.

EXAMPLE 2

6-Bromo-2-furan-2-yl-[1,2,4]triazolo[1,5-a]pyrazin-8-ylamine

Synthesis of the Title Compound is Described in Parts (a)-(c) Below.

(a) 1-Amino-3,5-dibromo-pyrazin-1-ium2,4,6-Trimethyl-benzenesulfonate

Trifluoroacetic acid (35 mL) was taken in a 100 mL RB flask with a magnetic stirrer. The t-butyl, O-mesitylene carbamate was added in small portions over 10 to 15 minutes. The resulting pale yellow solution was stirred for about half an hour, then slowly poured into approx. 100 g. of crushed ice with stirring when the O-mesitylene hydroxylamine precipitated out as a white solid. After about an hour, when all the ice melted, the white ppt. was filtered and washed thoroughly with water (5×25 mL). The solid was dissolved in 45 mL of CH$_2$Cl$_2$ and the residual water was removed (by pipette or seperatory funnel). The solution was dried over Na$_2$SO$_4$, filtered, and added slowly to a stirred solution of 2-amino, 3,5-dibromo pyrazine (7.1 g, Aldrich-Sigma, St, Louis, Mo.) in CH$_2$Cl$_2$ (35 mL). Within few minutes, off-white precipitate of the pyrazinum salt started separating out. The reaction was stirred for 20 hours and then cooled in ice/water bath (5-10° C.). The off-white precipitate was then filtered and washed with cold CH$_2$Cl$_2$ (3×8 mL) and dried in air to give 9.5 g. (73%) of relatively pure product which was analyzed by HPLC, MS, LC/MS and H$^1$ NMR.

(b) 2-Furan-2-yl-5-[4(5-methyl-isoxazol-3-ylmethyl)-piperazin-1-yl]-[1,2,4]triazolo[1,5-a][1,3,5]triazin-7-ylamine The 1,2-diamino-3,5-dibromopyrazinium salt described above (9.4 gm, 20 mmol) was dissolved in 150 mL of methanol in a 500 mL round bottom flask under nitrogen. 2-Furaldehyde (10 gm, 5.equiv.) was added to this solution. The reaction solution was stirred in a warm water bath (35-40° C.) for 24 hours. The methanol solvent was removed under reduced pressure and the brown residue (gummy mass) was triturated with 50 mL of ether. After settling the top ether layer was decanted off and the bottom gummy mass was triturated two more times with 25-30 mL of ether. The gummy residue was dissolved in 125-150 mL of warm dioxane and filtered. 2-Furan-2-yl-5-[4-(5-methyl-isoxazol-3-ylmethyl)-piperazin-1-yl]-[1,2,4]triazolo[1,5-a][1,3,5]triazin-7-ylamine (dissolved in dioxane) was used in the next step without further manipulation.

(c) 6-Bromo-2-furan-2-yl-[1,2,4]triazolo[1,5-a]pyrazin-8-ylamine

The dioxane solution containing 2-furan-2-yl-5-[4-(5-methyl-isoxazol-3-ylmethyl)-piperazin-1-yl]-[1,2,4]triazolo[1, 5-a][1,3,5]triazin-7-ylamine was cooled to about 10° C. (in an ice-bath) and anhydrous ammonia was bubbled through it for approximately 30 minutes; The reaction mixture was stirred at room temperature for overnight. The solvent was then removed under reduced pressure and the crude brown residue was triturated/extracted with EtOAc (3×50 mL). The extract was filtered and the solvent was removed to yield 10 g of crude brown product as a gummy syrup. The crude product was purified by flash chromatography using hexane/EtOAc (90/10; 80/20; 70/30) to yield 2.1 gm (38%) of 6-bromo-2-furan-2-yl-[1,2,4]triazolo[1,5-a]pyrazin-8-ylamine as a light brown solid. $^1$H NMR (300 MHz, CDCl$_3$) δ 6.70 (dd, 1H), 7.10 (d, 1H), 7.8-8.0 (br m, 3H), 8.58 (s, 1H). MS: m/z: 280 [M+H]$^+$.

EXAMPLE 3

2-Furan-2-yl-6-(5-phenyl-pent-1-ynyl)-[1,2,4]triazolo[1,5-a]pyrazin-8-ylamine

A solution of 6-bromo-2-furan-2-yl-[1,2,4]triazolo[1,5-a]pyrazin-8-ylamine (56 mg, 0.2 mmol; see Examples 1 and 2 above), pent-4-ynyl-benzene (44 mg, 0.3 mmol), Pd(PPh$_3$)$_4$ (26 mg, 0.03 mmol), CuI (4 mg, 0.03 mmol), PPh$_3$ (8 mg, 0.03 mmol), and TEA (11 μL, 2.5 mmol) in DMF (5 mL) was heated (at around 105° C.) under N$_2$ for 2 hours. The reaction was diluted with EtOAc (15 mL) and washed with brine (3×10 mL) and dried with MgSO$_4$. The solvent was removed and the reaction purified by HPLC (C18, H$_2$O:MeCN gradient) to afford the product as a brown solid (28 mg,). $^1$H NMR (400 MHz, DMSO-d$_6$) δ 1.85 (quin, J=7.5 Hz, 2H) 2.44 (t, J 7.1 Hz, 2H), 2.74 (t, J=7.8 Hz, 2H), 6.72 (dd, J=3.4, 1.8 Hz, 1H), 7.14 (dd, J=3.5, 0.8 Hz, 1H), 7.2-7.30 (br m, 5H), 7.92 (dd, J=1.7, 0.8 Hz, 1H), 8.35 (s, 1H). MS: m/z 344 [M+H]$^+$.

EXAMPLE 4

2-Furan-2-yl-6-(4-trifluoromethyl-phenyl)-[1,2,4]triazolo[1,5-a]pyrazin-8-ylamine A mixture of 6-bromo-2-furan-2-yl-[1,2,4]triazolo[1,5-a]pyrazin-8-ylamine (50 mg, 0.179; see Examples 1 and 2), 4-trifluoromethyl-phenyl boronic acid (0.196 mmol), Pd(dppf)Cl$_2$ (7 mg, 0.009 mmol), and aqueous Na$_2$CO$_3$ (2 M, 330 μL) in DMF (2 mL) was degassed under N$_2$ and then heated (at around 100° C.) for overnight. The reaction was filtered and then purified by HPLC (C18, H$_2$O:MeCN gradient). $^1$H NMR (300 MHz, DMSO-d$_6$) δ 6.77 (dd, J=3.4, 1.8 Hz, 1H), 7.19 (dd, J=3.4, 0.8 Hz, 1H), 7.70 (br. s, 2H), 7.87 (d, J=8.2 Hz, 2H), 7.93 (dd, J=1.8, 0.7 Hz, 1H), 8.31 (d, J=8.2 Hz, 2H), 8.8 (s, 1H). MS: m/z 346 [M+H]$^+$.

EXAMPLE 5

3-(8-Amino-2-furan-2-yl-[1,2,4]triazolo[1,5-a]pyrazin-6-yl)-benzoic acid

A mixture containing 3-(8-amino-2-furan-2yl-[1,2,4]triazolo[1,5-a]pyrazin-6-yl)-benzoic acid ethyl ester (100 mg; see Ex. 141 below, which was prepared according to Example 4 above), LiOH (2 M, 1 mL), and MeOH (a few drops) in THF (10 mL) was heated (at around 70° C.) for 1 hour. The solvent was removed in vacuo, and the residue was taken up in water and acidified, resulting in a precipitate, which was filtered off as the desired product with an appearance of a light brown solid (60 mg, 65 %). $^1$H NMR (300 MHz, DMSO-d$_6$) δ 6.76 (dd, J=3.4, 1.8Hz, 1H), 7.18 (dd, J=3.4, 0.8, 1H), 7.63 (t, J=7.9 Hz, 1H), 7.68 (br. s, 2H), 7.96 (dd, J=1.8, 0.8 Hz, 1H), 8.00 (dt, J=7.8, 1.8 Hz, 1H), 8.30 (dt, J=7.8, 1.8 Hz, 1H), 8.72 (t, J=1.8, 1H), 8.91 (s, 1H), 13.09 (br. s, 1 H). MS: m/z 322 [M+H]$^+$.

EXAMPLE 6

[3-(8-Amino-2-furan-2-yl-[1,2,4]triazolo[1,5-a]pyrazin-6-yl)-phenyl]-piperidin-1-yl-methanone A solution of 3-(8-amino-2-furan-2-yl-[1,2,4]triazolo[1,5-a]pyrazin-6-yl)-benzoic acid (20.mg, 0.063 mmol; see Example 5 above), HATU (30 mg, 0.095 mmol), piperdine (0.125 mmol), and diisopropylethylamine (11 µL, 0.063 mmol) in DMF (200 µL) was stirred at room temperature for 30 minutes. The solvent was removed, and the residue was purified by HPLC (C18, H$_2$O:MeCN gradient) to afford the product as a white solid (15 mg, 62%). $^1$H NMR (300 MHz, DMSO-d$_6$) δ 1.56 (br. s, 6H),3.35 (br. s,2H), 3.65 (br. s, 2H), 6.76 (dd, J=3.4, 1.7 Hz, 1H), 7.18 (dd, J=3.4, 0.8 Hz, 1H), 7.4 (br. dt, J=7.6, 1.4 Hz, 1H), 7.56 (t, J=7.6 Hz, 1H), 7.63 (br. s, 2H), 7.96 (dd, J=1.7, 0.8 Hz, 1H), 8.11 (br. s, 1H), 8.14 (dt, J=7.5, 1.5 Hz, 1H),8.9 (s, 1H).
MS: m/z 389 [M+1].

EXAMPLE 7

8-Amino-2-furan-2-yl-[1,2,4]triazolo[1,5-a]pyrazine-6-carboxylic acid methyl ester A solution containing 6-bromo-2-furan-2-yl-[1,2,4]triazolo[1,5-a]pyrazin-8-ylamine (2 g, 7.1 mmol; see Examples 1 and 2 above), Pd(OAc)$_2$ (639 mg, 2.8 mmol), 1,3-bis(diphenylphosphino)propane (1.28 g, 3.1 mmol), TEA (1.8 mL, 1.3 mmol), and MeOH (51 mL) in DMSO (148 mL) was degassed under a carbon monoxide atmosphere. The reaction was heated (80° C.) overnight under carbon monoxide (balloon). The solvent was removed in vacuo. The residue was purified by HPLC (C18, H$_2$O:MeCN gradient) to afford the titled compound as a light yellow solid (967 mg, 52%). $^1$H NMR (300 M DMSO-d$_6$) δ 3.86 (s, 3H), 6.73 (dd, J=3.4, 1.8 Hz, 1H), 7.19 (dd, J=3.4, 0.8 Hz, 1H), 7.80 (br. s, 2H), 7.95 (dd, J=1.8, 0.8 Hz, 1H), 8.71 (s, 1H). MS: m/z 260 [M+H]$^+$.

EXAMPLE 8

8-Amino-2-furan-2-yl-[1,2,4]triazolo[1,5-a]pyrazine-6-carboxylic acid

A mixture of 8-amino-2-furan-2-yl-[1,2,4]triazolo[1,5-a]pyrazine-6-carboxylic acid methyl ester (200 mg; see Example 7 above), LiOH (2 M, 1 mL), and MeOH (a few drops) in THF (20 mL) was heated (at around 70° C.) for 30 minutes. The solvent was removed in vacuo and then the residue was triturated with 0.5 N HCl. The product was dried to afford 8-amino-2-furan-2-yl-[1,2,4]triazolo[1,5-a]pyrazine-6-carboxylic acid as a light yellow solid (128 mg, 67%). $^1$H NMR (300 MHz, DMSO-d$_6$) δ 6.73(dd, J=3.5, 1.8 Hz, 1H), 7.18(dd, J=3.5, 0.9 Hz, 1H), 7.7(br. s, 2H), 7.94(dd, J=1.8, 0.8 Hz, 1H), 8.68(s, 1H). MS: m/z 246 [M+H]$^+$.

EXAMPLE 9

(8-Amino-2-furan-2-yl-[1,2,4]triazolo[1,5-a]pyrazin-6-yl)-carbamic acid tert-butyl ester A mixture containing 8-amino-2-furan-2-yl-[1,2,4]triazolo[1,5-a]pyrazine-6-carboxylic acid (100 mg, 0.41 mmol; see Example 8 above), TEA (209 µL, 1.5 mmol), t-BuOH (1.5 mL) and diphenylphosphoryl azide (339 µl, 1.6 mmol) in DMF (1.5 ml) was heated (at around 80° C.) overnight. The solvent was removed in vacuo and the residue was purified by HPLC (C18, H$_2$O:MeCN gradient) to afford the product as a yellow solid (20 mg, 16%). $^1$H NMR (300 MHz, CDCl$_3$) δ 1.56 (s, 9H), 5.92 (br. s, 2H), 6.58 (dd, J=3.4, 1.8 Hz, 1H), 7.15 (dd, J=3.4, 0.8 Hz, 1H), 7.62 (dd J=1.8, 0.8 Hz, 1H), 8.61 (br. s, 1H). MS: m/z 317 [M+H]$^+$.

EXAMPLE 10

(8-Diacetylamino-2-furan-2-yl-[1,2,4]triazolo[1,5-a]pyrazin-6-yl)-carbamic acid tert-butyl ester A mixture of (8-amino-2-furan-2-yl-[1,2,4]triazolo[1,5-a]pyrazin-6-yl)-carbamic acid tert-butyl ester (9 mg; see Example 9 above) and Ac$_2$O (125 µL) in pyridine (250 µL) was heated (70° C.) overnight. The solvent was removed and the reaction we purified by HPLC (C18, H$_2$O:MeCN gradient. MS: m/z 401 [M+H]$^+$.

EXAMPLE 11

8-Amino-2-furan-2-yl-[1,2,4]triazolo[1,5-a]pyrazine-6-carboxylic acid diethylamide A solution of 8-amino-2-furan-2-yl-[1,2,4]triazolo[1,5-a]pyrazine-6-carboxylic acid (20 mg, 0.082 mmol; see Example 8 above), diisopropylethylamine (14 µL, 0.082 mmol), HATU (47 mg, 0.123 mmol), and diethylamine (0.163 mmol) in DMF (300 µL) was stirred at room temperature for 1 hour. The solvent was removed in vacuo. The residue was purified by HPLC (C18, H$_2$O:MeCN gradient). $^1$H NMR (300 MHz, DMSO-d$_6$) δ 1.17 (t, J=6.9 Hz, 6H), 3.41 (m, 4H), 6:76 (dd, J3.4, 1.7 Hz, 1H), 7.18 (dd, J=3.4, 0.7 Hz, 1H), 7.69 (br. s, 2H), 7.96 (dd, J=1.7, 0.7 Hz, 1H), 8.34 (s, 1H). MS: m/z 301 (M+1).

EXAMPLE 12

4-[3-(8-Amino-2-furan-2-yl-[1,2,4]triazolo[1,5-a]pyrazin-6-yl)-prop-2-ynyl]-piperazine-1-carboxylic acid tert-butyl ester Synthesis of the title compound is described in parts (a) and (b) below.

a) 4-Prop-2-ynyl-piperazine-1-carboxylic acid tert-butyl ester

To a vigorously stirred suspension of piperazine-1-carboxylic acid tert-butyl ester (4.2 g, 22.5 mmol) and K$_2$CO$_3$ (1.2 eq, 27 mmol, 3.7 g) was added propargyl bromide (80 wt % in toluene, 1.2 eq, 27 mmol) dropwise via syringe over 20 minutes. The mixture was stirred at room temperature overnight (about 20 hours), concentrated in vacuo and partitioned between water and EtOAc. The organic-phase was washed twice with water, dried over MgSO$_4$, filtered and evaporated to afford a clear yellow oil that partially solidified upon prolonged standing and was used directly without further purification. $^1$H NMR (400 MHz, CDCl$_3$) d 1.47 (s, 9H), 2.28 (t, 1H), 2.54 (m, 4H), 3.34 (d, 2H, J=2.4 Hz), 3.49 (m, 4H). MS: m/z 225 (M+1).

b) 4-[3-(8-Amino-2-furan-2-yl-[1,2,4]triazolo[1,5-a]pyrazin-6-yl)-prop-2-ynyl]-piperazine-1-carboxylic acid tert-butyl ester 4-[3-(8-Amino-2-furan-2-yl-[1,2,4]triazolo[1,5-a]pyrazin-6-yl)-prop-2-ynyl]-piperazine-1-carboxylic acid tert-butyl ester was prepared in an analogous manner as described in Example 3. $^1$H NMR (400 MHz, CDCl$_3$) d 1.47 (s, 9H), 2.54 (m, 4H), 3.28 (m, 4H), 3.59 (m, 2H), 6.73 (dd, 1H), 7.25 (dd, 1H), 7.62 (brs, 2H), 7.94 (m, 1H), 8.43 (s, 1H). MS: m/z 424 (M+1).

EXAMPLE 13

4-[3-(8-Amino-2-furan-2-yl-[1,2,4]triazolo[1,5-a]pyrazin-6-yl)-propyl]-piperazine-1-carboxylic acid tert-butyl ester To a stirred solution of 4-[3-(8-amino-2-furan-2-yl-[1,2,4]triazolo[1,5-a]pyrazin-6-yl)-prop-2-ynyl]-piperazine-1-carboxylic acid tert-butyl ester (20 mg; see Example 12 above) in EtOH (1 mL) was added palladium (10 wt.% on activated carbon, ca. 5 mg). The reaction mixture was hydrogenated (45 psi) overnight, filtered through Celite and concentrated in vacuo. The resulting oil was purified by radial chromatography using 5% MeOH/CH2Cl2as eluent to afford the title compound. $^1$H NMR (400 MHz, CDCl$_3$) δ 1.45 (s, 9H), 1.94 (m, 2H), 2.44 (m, 4H), 2.65 (t, 2H), 3.45 (m, 4H), 5.67 (s, 2H), 6.57 (dd, 1H), 7.13 (dd, 1H), 7.60 (s, 1H), 7.76 (s, 1H).

EXAMPLE 14

2-Furan-2-yl-6-methanesulfonyl-[1,2,4]triazolo[1,5-a]pyrazin-8-ylamine

Synthesis of the title compound is described in parts (a)-(d) below.

(a) 2-(8-Amino-2-furan-2-yl-[1,2,4]triazolo[1,5-a]pyrazin-6-yl)-isothiourea

A solution of 6-bromo-2-furan-2-yl-[1,2,4]triazolo[1,5-a]pyrazin-8-ylamine (100 mg, 0.357 mmol; see Examples 1 and 2 above) and H$_2$SO$_4$ conc. (10 drops) in EtOH (4 mL) was refluxed for 2 hours. The solvent was removed in vacuo to yield the crude product 2-(8-amino-2-furan-2-yl-[1,2,4]triazolo[1,5-a]pyrazin-6-yl)-isothiourea, which was used in the next step without purification.

(b) 8-amino-2-furan-2-yl-[1,2,4]triazolo[1,5-a]pyrazine-6-thiol

A solution containing the crude 2-(8-amino-2-furan-2-yl-[1,2,4]triazolo[1,5-a]pyrazin-6-yl)-isothiourea and aqueous KOH (1 M, 4 ml) was refluxed for 1 hour. The reaction was neutralized with conc. HCl and the water was removed in vacuo to afford the crude product 8-amino-2-furan-2-yl-[1,2,4]triazolo[1,5-a]pyrazine-6-thiol, which was used in the next step without purification.

(c) 2-Furan-2-yl-6-methylsulfanyl-[1,2,4]triazolo[1,5-a]pyrazin-8-ylamine

A mixture containing the crude 8-amino-2-furan-2-yl-[1,2,4]triazolo[1,5-a]pyrazine-6-thiol, K$_2$CO$_3$ (199 mg), and MeI (162 μL) in DMF (8 mL) was stirred at room temperature for 1 hour. The solvent was removed in vacuo and the residue was taken up in EtOAc and passed through a plug of silica. The solvent was removed in vacuo and the residue was triturated with H$_2$O to afford 2-furan-2-yl-6-methylsulfanyl-[1,2,4]triazolo[1,5-a]pyrazin-8-ylamine as a brown solid (54 mg, 61% from the bromide).

(d) 2-Furan-2-yl-6-methanesulfonyl-[1,2,4]triazolo[1,5-a]pyrazin-8-ylamine

A solution of the 2-furan-2-yl-6-methylsulfanyl-[1,2,4]triazolo[1,5-a]pyrazin-8-ylamine (20 mg, 0.081 mmol) and m-CPBA (45 mg, 0.26 mmol) in CH$_2$Cl$_2$ (1 mL) was stirred for 20 minutes at room temperature. The reaction was washed with aqueous Na$_2$CO$_3$ (2 M), dried (with Na$_2$SO$_4$) and evaporated to afford 2-furan-2-yl-6-methanesulfonyl-[1,2,4]triazolo[1,5-a]pyrazin-8-ylamine as a light yellow solid (15 mg, 66%). $^1$H NMR (300 MHz, DMSO-d$_6$) δ 6.6 (dd, J=3.4, 1.8 Hz, 1H), 7.19 (dd, J=3.4, 0.8 Hz, 1H), 7.8 (s, 1H), 7.95 (br. s, 2H), 8.5 (s, 1H). MS: m/z 280 [M+H]$^+$.

EXAMPLE 15

2-Furan-2-yl-6-iodo-[1,2,4]triazolo[1,5-a]pyrazin-8-ylamine

A solution of 6-bromo-2-furan-2-yl-[1,2,4]triazolo[1,5-a]pyrazin-8-ylamine (600 mg; see Examples 1 and 2 above) and 57% HI (10 mL) in EtOH (50 mL) was refluxed for 1 hour. The solvent was removed in vacuo and the residue was triturated with H$_2$O to afford 2-furan-2-yl-6-iodo-[1,2,4]triazolo[1,5-a]pyrazin-8-ylamine as a brown solid (642 mg, 92%). $^1$H NMR (300 MHz, DMSO-d$_6$) δ 6.8 (dd, J3.4, 1.8 Hz, 1H), 7.2 (dd, J=3.4, 0.8 Hz, 1H), 7.95 (s, 1H), 8.6 (s, 1H). MS: m/z 327 [M+H]$^+$.

EXAMPLE 16

2-Furan-2-yl-6-piperazin-1-yl-[1,2,4]triazolo[1,5-a]pyrazin-8-ylamine

Synthesis of the title compound is described in parts (a)-(j) below.

(a) Methyl 3-amino-6-bromo-2-pyrazine-carboxylate

Methyl 3-amino-2-pyrazine-carboxylate (10 g, 65.3 mmol) was dissolved in glacial acetic acid (50 mL) by warming to approximately 45° C. To the warm solution was added bromine (3.7 mL) in acetic acid (5 mL) dropwise and the resulting mixture was stirred at room temperature for 20 minutes. The solution was diluted with water (300 mL) and then stirred at room temperature for 30 minutes, which resulted in a precipitate. The precipitate was then filtered, washed with water and dried to afford methyl 3-amino-6-bromo-2-pyrazine-carboxylate as a yellow solid (14.2 g, 94%). $^1$H NMR (300 MHz, CDCl$_3$) δ3.99 (s, 3H), 8.30 (s, 1 H); $^{13}$C NMR (100 MHz, CDCl$_3$) δ 53.02, 123.49, 124.85, 150.24, 154.70, 166.04.

(b) 3-Amino-6-bromo-pyrazine-2-carboxylic acid methylamide

Methyl 3-amino-6-bromo-2-pyrazine-carboxylate (14.3 g, 61.6 mmol; see Example 16 (a) above) was suspended in 40% aqueous methylamine (350 mL) and the resulting mixture was stirred vigorously for 7 hours at room temperature. The precipitate was collected, washed with water, and dried to afford 3-amino-6-bromo-pyrazine-2-carboxylic acid methylamide as a yellow solid (12.7 g, 90%). $^1$H NMR (300 MHz, DMSO-d$_6$) δ2.77 (d, J=3 Hz, 3H), 7.70 (br s, 2H), 8.33 (s, 1H), 8.56 (q, J=3 Hz, 1 H); $^{13}$C NMR (100 MHz, DMSO-d$_6$) δ27.84, 123.49, 127.69, 150.43, 156.04, 167.18.

(c) 6-Bromo-3-methyl-3H-pteridin-4-one

To a mixture of triethyl orthoformate (70 mL) and acetic anhydride (70 mL) was added 3-amino-6-bromo-pyrazine-2-carboxylic acid methylamide (12.7 g, 55 mmol; see Example 16 (b) above) with stirring. The resulting solution was heated at reflux for 2 hours and allowed to cool to room temperature. The precipitate that formed was collected, washed with ethyl acetate, and dried to afford 6-bromo-3-methyl-3H-pteridin-4-one as a white solid (11.8 g, 89%). $^1$H NMR (300 MHz, DMSO-d$_6$) δ3.54 (s, 3H), 8.70 (s, 1H), 9.15 (s, 1 H); $^{13}$C NMR (100 MHz, DMSO-d$_6$) δ34.03, 133.28, 137.82, 152.39, 152.70, 153.33, 159.19.

(d) 4-(3-Methyl-4-oxo-3,4-dihydro-pteridin-6-yl)-piperazine-1-carboxylic acid tert-butyl ester To a stirred solution of 1-Boc-piperazine (18.9 g, 101.4 mmol) in 2-methoxyethanol (100 mL) was added 6-bromo-3-methyl-3H-pteridin-4-one (11.6 g, 48 mmol; see Example 16 (c) above) and the resulting suspension was heated for 3 hours at 100° C. The reaction was then cooled in an ice-water bath and the precipitate that formed was collected, washed with cold MeOH, and dried to afford 4-(3-methyl-4-oxo-3,4-dihydro-pteridin-6-yl)-piperazine-1-carboxylic acid tert-butyl ester as a yellow solid (15.2 g, 92%). $^1$H NMR (300 MHz, CDCl$_3$) δ1.48 (s, 9H), 3.57-3.61 (m, 4H), 3.62 (s, 3H),3.78-3.82 (m, 4H), 8.07 (s, 1H), 8.56 (s, 1 H); $^{13}$C NMR (100 MHz, CDCl$_3$) δ28.38, 34.42, 44.40, 80.38, 130.64, 137.93, 145.53, 147.04, 152.91, 154.61, 160.89.

(e) 5'-Amino-2,3,5,6-tetrahydro-[1,2']bipyrazinyl-4, 6'-dicarboxylic acid 4-tert-butyl ester To a stirred suspension of 4-(3-methyl-4-oxo-3,4-dihydro-pteridin-6-yl)-piperazine-1-carboxylic acid tert-butyl ester (428 mg, 1.24 mmol; see Example 16 (d) above) in methanol (5 mL) was added 10% aqueous sodium hydroxide (5 mL). The reaction mixture was stirred overnight at room temperature and concentrated in vacuo. The residue was then diluted with water and neutralized with formic acid (pH 7). The resulting precipitate was removed by filtration and the filtrate was acidified with formic acid (pH 4) and extracted with methylene chloride. The combined organic phases were washed with brine, dried over anhydrous magnesium sulfate, and concentrated in vacuo to afford 5'-amino-2,3,5,6-tetrahydro-[1,2']bipyrazinyl-4,6'-dicarboxylic acid 4tert-butyl ester as a yellow solid (265 mg, 67%). $^1$H NMR (300 MHz, CDCl$_3$) δ1.49 (s, 9 H), 3.38 (t, J=5.4 Hz, 4H), 3.60 (t, J=5.4 Hz, 4H), 6.06 (br s, 1H), 8.15 (s, 1H); $^{13}$C NMR (75 MHz, CDCl$_3$) δ28.39, 46.16, 80.29, 116.40, 138.73, 147.39, 149.67, 154.59, 165.95.

(f) 5'-Amino-2,3,5,6-tetrahydro-[1,2']bipyrazinyl-4, 6'-dicarboxylic acid 4-tert-butyl ester 6'-methyl ester To a solution of 5'-amino-2,3,5,6-tetrahydro-[1,2']bipyrazinyl-4,6'-dicarboxylic acid 4-tert-butyl ester (510 mg, 1.6 mmol; see Example 16 (e) above) in benzene (4 mL) and methanol (4 mL) was added a solution of trimethylsilyldiazomethane (2 M in hexane, 2 mL). The reaction was stirred at room temperature for overnight. The solvent was then removed in vacuo and the residue was purified by flash chromatography using ethyl acetate/hexanes (40:60) as eluant to afford 5'-amino-2,3,5,6-tetrahydro-[1,2']bipyrazinyl-4,6'-dicarboxylic acid 4-tert-butyl ester 6'-methyl ester as a yellow solid (520 mg, 96%). $^1$H NMR (300 MHz, CDCl$_3$) δ1.49 (s, 9H), 3.40 (s, 4H), 3.59 (s, 4H), 3.95 (s, 3H), 8.01 (s, 1 H); $^{13}$C NMR (100 MHz, CDCl$_3$) δ 28.41, 46.30, 52.52, 80.05, 119.69, 135.58, 148.24, 150.00, 154.70, 167.10.

(g) 6-(4-tert-Butoxycarbonyl-piperazin-1-yl)-2-furan-2-yl-[1,2,4]triazolo[1,5-a]pyrazine-8-carboxylic acid methyl ester t-Butyl-N-mesitylenesulfonyloxy carbamate (26.46 g, 84 mmol) was added portionwise to trifluoroacetic acid (83 mL) and the resulting solution was stirred at room temperature for 1 hour. The reaction mixture was poured onto crushed ice (300 g) with stirring. The white solid that formed was collected and washed with water. White still wet the precipitate was dissolved in methylene chloride (100 mL) and transferred to a separatory funnel to assist removal of the residual water. The organic phase was dried over anhydrous magnesium sulfate, filtered, and then added slowly to a stirred solution of 5'-amino-2,3,5,6-tetrahydro-[1,2']bipyrazinyl-4,6'-dicarboxylic acid 4-tert-butyl ester 6'-methyl ester (5.66 g, 16.8 mmol; see Example 16 (f) above) in methylene chloride (70 mL). After the resulting solution was stirred at room temperature overnight, the mixture was concentrated to give a red solid. The red solid was dissolved in 1,4-dioxane (140 mL) and 2-furaldehyde (1.53 mL, 18.5 mmol) was added to this solution. The reaction mixtures was stirred at 100° C. for 3 hours. After the solvent was removed, the residue was subjected to flash chromatography using ethyl acetate/hexanes (40:60, 50:50) as eluant to afford 6-(4-tert-butoxycarbonyl-piperazin-1-yl)-2-furan-2-yl-[1,2,4]triazolo[1,5-a]pyrazine-8-carboxylic acid methyl ester as a yellow solid (658 mg 9%). $^1$H NMR (300 MHz, CDCl$_3$) δ1.50 (s, 9H), 3.49 (dd, J=4.8, 5.4 Hz, 4H), 3.65 (dd, J=4.8, 5.4 Hz, 4H), 4.12 (s, 3H), 6.59 (dd, J=1.8, 3.3 Hz, 1H), 7.29 (d, J=3.3 Hz, 1H), 7.63 (d, J=1.8 Hz, 1H), 8.04 (s, 1 H); $^{13}$C NMR (100 MHz, CDCl$_3$) δ28.40, 46.05, 53.54, 80.30, 106.46, 112.01, 112.81, 136.63, 142.42, 144.73, 145.43, 148.48, 154.58, 157.98, 162.75.

(h) 6-(4-tert-Butoxycarbonyl-piperazin-1-yl)-2-furan-2-yl-[1,2,4]triazolo[1,5-a]pyrazine-8-carboxylic acid A solution of 6-(4-tert-butoxycarbonyl-piperazin-1-yl)-2-furan-2-yl-[1,2,4]triazolo[1,5-a]pyrazine-8-carboxylic acid methyl ester (4 mg, 0.009 mmol; see Example 16 (g) above) in 1 N potassium hydroxide methanol solution (1 mL) was stirred at room temperature for 2 hours. The solvent was then removed, and the residue was suspended in water. The resulting suspension was acidified with acetic acid until pH 4 and extracted with methylene chloride three times. The combined organic phases were washed with brine, dried over anhydrous magnesium sulfate, and concentrated to afford 6-(4-tert-butoxycarbonyl-piperazin-1-yl)-2-furan-2-yl-[1,2,4]triazolo[1, 5-a]pyrazine-8-carboxylic acid as a yellow solid (2.6 mg, 68%). $^1$H NMR (300 MHz, CDCl$_3$) δ1.50 (s, 9H), 3.53-3.58 (m, 4H), 3.63-3.68 (m, 4H), 6.63 (dd, J=1.8, 3.3 Hz, 1H), 7.35 (d, J=3.3 Hz, 1H), 7.67 (d, J=1.8 Hz, 1H), 8.08 (s, 1 H); $^{13}$C NMR (100 MHz, CDCl$_3$) δ28.39, 45.90, 80.49, 106.62, 112.27, 113.83, 134.92, 142.08, 144.56, 145.30, 149.18, 154.60, 157.09, 161.49.

(i) 4-(8-tert-Butoxycarbonylamino-2-furan-2-yl-[1,2,4]triazolo[1,5-a]pyrazin-6-yl)-piperazine-1-carboxylic acid tert-butyl ester To a solution containing 6-(4-tert-butoxycarbonyl-piperazin-1-yl)-2-furan-2-yl-[1,2,4]triazolo[1,5-a]pyrazine-8-carboxylic acid (223 mg, 0.54 mmol; see Example 16 (h) above) and triethylamine (188 μL) in t-butyl alcohol (11 mL) was added diphenylphosphoryl azide (140 μL). After the mixture was heated at reflux under nitrogen for 7 hours, the solvent was removed. The residue was dissolved in methylene chloride, washed with brine, dried over anhydrous magnesium sulfate, and concentrated. The resulting residue was subjected to flash chromatography (ethyl acetate/hexanes 20:80, 30:70) to afford 4-(8-tert-butoxycarbonylamino-2-furan-2-yl-[1,2,4]triazolo[1,5-a]pyrazin-6-yl)-piperazine-1-carboxylic acid-tert-butyl ester (140 mg, 54%) and a smaller amount of 4-(8-amino-2-furan-2-yl-[1,2,4]triazolo[1,5-a]pyrazin-6-yl)-piperazine-1-carboxylic acid tert-butyl ester (29 mg, 15%) as yellow solids.

4-(8-tert-Butoxycarbonylamino-2-furan-2-yl-[1,2,4]triazolo[1,5-a]pyrazin-6-yl)-piperazine-1-carboxylic acid tert-butyl ester: $^1$H NMR (300 MHz, CDCl$_3$) δ1.41 (s, 9H), 1.46 (s, 9H), 3.33 (t, J=3 Hz, 4H), 3.53 (t, J=3 Hz, 4H), 6.48 (d, J=3 Hz, 1H), 7.01 (d, J=3 Hz, 1H), 7.51 (s, 1H), 8.09 (s, 1 H); $^{13}$C NMR (75 MHz, CDCl$_3$) δ 14.06, 28.05, 28.31, 46.01, 60.19, 79.89, 81.97, 97.70, 110.82, 111.70, 135.17, 140.04, 143.97, 145.66, 148.27, 149.32, 154.52, 155.46. 4-(8-Amino-2-furan-2-yl-[1,2,4]triazolo[1,5-a]pyrazin-6-yl)-piperazine-1-carboxylic acid tert-butyl ester: $^1$H NMR (300 MHz, CDCl$_3$) δ1.46 (s, 9H), 3.25-3.28 (m, 4H), 3.55-3.58 (m, 4H), 6.53 (dd, J=1.8, 3.3 Hz, 1H), 7.06 (d, J=3.3 Hz, 1H), 7.23 (d, J=1.8 Hz, 1H), 7.56 (s, 1 H).

(j) 2-Furan-2-yl-6-piperazin-1-yl-[1,2,4]triazolo[1,5-a]pyrazin-8-ylamine

To a solution of 4-(8-tert-butoxycarbonylamino-2-furan-2-yl-[1,2,4]triazolo[1,5-a]pyrazin-6-yl)-piperazine-1-carboxylic acid tert-butyl ester (140 mg, 0.29 mmol; see Example 16 (i) above) in methylene chloride (4 mL) was added trifluoroacetic acid (400 μL). The reaction was stirred at room temperature for 2 hours. After the solvent and extra trifluoroacetic acid was evaporated, the residue was dissolved in methylene chloride (4 mL). The title compound in methylene chloride was divided into two portions and used for further reactions (see Example 17 and Example 18 below) without further purification.

EXAMPLE 17

2-Furan-2-yl-6-[4-(2,4,6-trifluoro-benzyl)-piperazin-1-yl]-[1,2,4]triazolo[1,5-a]pyrazin-8-ylamine To a solution of 2-furan-2-yl-6-piperazin-1-yl-[1,2,4]triazolo[1,5-a]pyrazin-8-ylamine in methylene chloride (see Example 16 above) was added 2,4,6-trifluorobenzaldehyde (28 mg, 0.18 mmol), sodium triacetoxyborohydride (46 mg, 0.22 mmol) and acetic acid (6 μL, 0.1 mmol). The reaction was stirred at room temperature for overnight. After the solvent was removed, the residue was subjected to flash chromatography (ethyl acetate/hexanes=30:70, 40:60) to afford 2-furan-2-yl-6-[4-(2,4,6-trifluoro-benzyl)-piperazin-1-yl]-[1,2,4]triazolo[1,5-a]pyrazin-8-ylamine as a white solid (35 mg, 56%). $^1$H NMR (300 MHz, CDCl$_3$) δ2.66 (t, J=4.5 Hz, 4H), 3.34 (t, J=4.5 Hz, 4H), 3.73 (s, 2H), 5.61 (s, 2H), 6.54 (dd, J=1.8, 3.6 Hz, 1H), 6.67 (d, J=7.8 Hz, 1H), 6.70 (d, J=7.8 Hz, 1H), 7.07 (d, J=3.6 Hz, 1H), 7.26 (s, 1H), 7.57 (d, J=1.8 Hz, 1H); $^{13}$C NMR (100 MHz, CDCl$_3$) δ46.53, 48.35, 51.56, 95.63, 99.82, 100.10, 100.38, 110.29, 111.73, 134.80, 143.80, 146.00, 146.42, 149.06, 155.13.

EXAMPLE 18

6-[4-(5-Chloro-1-methyl-3-trifluoromethyl-1H-pyrazol-4-ylmethyl)-piperazin-1-yl]-2-furan-2-yl-[1,2,4]triazolo[1,5-a]pyrazin-8-ylamine To a solution of 2-furan-2-yl-6-piperazin-1-yl-[1,2,4]triazolo[1,5-a]pyrazin-8-ylamine in methylene chloride (see Example 16 above) was added 5-chloro-1-methyl-3-(trifluoromethyl)pyrazole-4-carboxaldehyde (45 mg, 0.21 mmol), sodium triacetoxyborohydride (65 mg, 0.31 mmol) and acetic acid (12 μL, 0.2 mmol). The reaction was stirred at room temperature overnight. After the solvent was removed, the residue was subjected to flash chromatography (ethyl acetate/hexanes=40:60) to afford 6-[4-(5-chloro-1-methyl-3-trifluoromethyl-1H-pyrazol-4-ylmethyl)-piperazin-1-yl]-2-furan-2-yl-[1,2,4]triazolo[1,5-a]pyrazin-8-ylamine as a white solid (9 mg, 13%).

$^1$H NMR (300 MHz, CDCl$_3$) δ2.62-2.70 (m, 4H), 3.27-3.39 (m, 4H), 3.54 (s, 2H), 3.92 (s, 3H), 5.54 (s, 2H), 6.56 (dd, J=1.8, 3.3 Hz, 1H), 7.08 (d, J=3.3 Hz, 1H), 7.27 (s, 1H), 7.58 (d, J=1.8 Hz, 1H). MS: m/z 482.14 [M+H]$^+$.

EXAMPLE 19

5-(8-Amino-2-furan-2-yl-[1,2,4]triazolo[1,5-a]pyrazin-6-yl)-1H-pyridin-2-one

A solution of 2-furan-2-yl-6-(6-methoxy-pyridin-3-yl)-[1,2,4]triazolo[1,5-a]pyrazin-8-ylamine (25 mg; see Ex. 201 below which was prepared according to Example 4 above), MeOH (100 uL) and conc. HCl (100 uL) in dioxane (2 mL) was heated (around 90 C) for 1 hour. The solvent was removed and the residue was triturated with water to afford 5-(8-amino-2-furan-2-yl-[1,2,4]triazolo[1,5-a]pyrazin-6-yl)-1H-pyridin-2-one (19 mg, 80%) as a brown solid. $^1$H NMR, (400 MHz, DMSO-d$_6$) δ6.47 (dd, J=9.6, 0.6 Hz, 1H), 6.72 (dd, J=3.4, 1.9 Hz, 1H), 7.12 (dd, J=3.4, 0.6 Hz, 1H), 7.92 (dd, J=1.8, 0.9 Hz, 1H), 8.07 (dd, J=2.6, 0.6 Hz, 1H), 8.11 (dd, J=9.4, 2.6 Hz, 1H), 8.18 (s, 1H). MS: m/z 295 [M+1].

EXAMPLE 20

N-[3-(8-Amino-2-furan-2-yl-[1,2,4]triazolo[1,5-a]pyrazin-6-yl)-prop-2-ynyl]-N-methyl-isonicotinamide To a solution of 2-furan-2-yl-6-(3-methylamino-prop-1-ynyl)-[1,2,4]triazolo[1,5-a]pyrazin-8-ylamine (0.05 mmol, see Ex. 42 below which was prepared according to Example 3 above) in DMF (200 uL) was added isonicotinic acid (7 mg, 0.05 mmol), EDC (14.5 mg, 0.05 mmol), HOBT (6.8 mg, 0.05 mmol) and TEA (100 uL) successively. The reaction was stirred overnight, diluted with water, and extracted with methylene chloride. The combined organic extracts were washed with brine, dried over magnesium sulfate and concentrated in vacuo. The residue was purified using preparative HPLC (C18, H$_2$O:MeCN gradient) to afford the desired product as a TFA salt. $^1$H NMR (300 MHz, Acetone-d$_6$) δ8.78 (br. s, 2H), 8.31 (s, 1 H), 7.90 (d, J=2.1 Hz, 1H), 7.80 (br, s 2H), 7.13 (d, J=3.3 Hz, 1H), 7.04 (br. S. 1H), 6.67 (dd, J=2.1 Hz, 3.3 Hz, 1H), 4.65 (s, 1H), 4.34 (s, 1H), 3.63-3.14 (br. s, 3H). MS: m/z 374 [M+1].

EXAMPLE 21

Thiophene-3-sulfonic acid [3-(8-amino-2-furan-2-yl-[1,2,4]triazolo[1,5-a]pyrazin-6-yl)-prop-2-ynyl]-amide To a solution of 6-(3-amino-prop-1-ynyl)-2-furan-2-yl-[1,2,4]triazolo[1,5-a]pyrazin-8-ylamine (0.1 mmol, see Example 26 below) in THF (1 mL) was added thiophene-3-sulfonyl chloride (23.7 mg, 0.13 mmol), a catalytic quantity of DMAP and Hünig's base (52 uL, 0.3 mmol) successively. The reaction was stirred overnight and diluted with water. The aqueous layer was extracted with methylene chloride. The combined organic extracts were washed with brine and dried over magnesium sulfate. The solvent was then evaporated. The residue was purified using preparative HPLC (C18, $H_2O$: MeCN gradient) to afford the desired product. $^1$H NMR (400 MHz, DMSO-$d_6$) δ8.16 (1H), 8.09 (1H), 7.86 (1H), 7.68 (1H), 7.54 (1H), 7.31 (1H), 7.07(1H), 6.65 (1H), 4.23 (2H), 3.53 (d, J=7 Hz, 2H). MS: m/z 401 [M+1].

EXAMPLE 22

2-Furan-2-yl-6-(3-phenoxy-prop-1-ynyl)-[1,2,4]triazolo[1,5-a]pyrazin-8-ylamine

A solution of phenol (9.4 mg, 0.1 mmol) and 3-(8-amino-2-furan-2-yl-[1,2,4]triazolo[1,5-a]pyrazin-6-yl)-prop-2-yn-1-ol (0.05 mmol, see Ex. 46 below which was prepared according to Example 3 above) in THF (1 mL) at 0° C. was treated with triphenyl phosphine (26 mg, 0.1 mmol) and diisopropyl azodicarboxylate (20 uL, 0.1 mmol). After 30 min at 0° C., the reaction was allowed to warm to room temperature and was stirred for an additional 14 hours. The reaction mixture was diluted with water and concentrated in vacuo. The aqueous phase was extracted with ethyl acetate, and the organic extract was washed with brine, dried over magnesium sulfate, and concentrated in vacuo. The residue was purified using preparative HPLC (C18, $H_2O$:MeCN gradient) to afford 2-furan-2-yl-6-(3-phenoxy-prop-1-ynyl)-[1,2,4]triazolo[1,5-a]pyrazin-8-ylamine as a white powder. $^1$H NMR (300 MHz, DMSO-$d_6$) δ 8.45 (s, 1H), 7.92 (d, 1H), 7.34 (br m, 2H), 7.34 (t, J=8.7 Hz, 2H) 7.14 (d, J=3 Hz, 1H), 7.0-7.1 (br m, 3H), 6.72 (dd, J=3.0, 1.8 Hz, 1H), 5.07 (s, 2H), MS: m/z 332 [M+1].

EXAMPLE 23

2-Furan-2-yl-6-(3-phenyl-3-phenylamino-prop-1-ynyl)-[1,2,4]triazolo[1,5-a]pyrazin-8-ylamine Synthesis-of the title compound is described in parts (a)-(b) below.

a) 6-Ethynyl-2-furan-2-yl-[1,2,4]triazolo[1,5-a]pyrazin-8-ylamine

To a stirred solution of 6-bromo-2-furan-2-yl-[1,2,4]triazolo[1,5-a]pyrazin-8-ylamine (500 mg, 1.78 mmol, see Examples 1 and 2 above) and (trimethylsilyl)acetylene (1.5 mL, 10 mmol) in a mixture of THF (10 mL) and TEA (5 mL) was added copper(I) iodide (68 mg, 0.36 mmol, 20 mol %) and $PdCl_2(PPh_3)_2$ (190 mg, 0.27 mmol, 15 mol %). The reaction vessel was degassed and heated at 50° C. for 18 hours. After cooling to room temperature, the reaction mixture was diluted with water and extracted with methylene chloride. The combined organic extracts were dried over magnesium sulfate, and concentrated in vacuo to yield a crude product, which was purified by flash chromatography (silica gel, elution with 20% to 40% EtOAc/Hexane in volume) to afford the resulting 2-furan-2-yl-6-trimethylsilanylethynyl-[1,2,4]triazolo[1,5-a]pyrazin-8-ylamine. The trimethylsilyl group was removed by treating a stirred solution of the crude material (2-furan-2-yl-6-trimethylsilanylethynyl-[1,2,4]triazolo[1,5-a]pyrazin-8-ylamine) in wet MeOH (20 mL) with Amberlyst A26 resin (2 g) for 1 hour. The suspension was filtered, and the resin was washed, sequentially with MeOH and THF. The filtrate was concentrated in vacuo to yield the desired 6-ethynyl-2-furan-2-yl-[1,2,4]triazolo[1,5-a]pyrazin-8-ylamine (0.34 mg, 84% overall yield), which was used in the subsequent transformation without further purification.

b) 2-Furan-2-yl-6-(3-phenyl-3-phenylamino-prop-1-ynyl)-[1,2,4]triazolo[1,5-a]pyrazin-8-ylamine To a solution of benzylidene-phenyl-amine (0.05 mmol) (prepared by heating neat phenylamine (0.05 mmol) and benzaldehyde (0.05 mmol) at 60° C. for 2 hours) in a 1:1 mixture of THF (250 uL) and methanol (250 uL) was added the above 6-ethynyl-2-furan-2-yl-[1,2,4]triazolo[1,5-a]pyrazin-8-ylamine (11 mg, 0.05 mmol). CuBr (2.2 mg, 0.015 mmol, 30 mol %) was added to the reaction mixture followed by $RuCl_3$ (0.03 mg, 0.0015, 3 mol %) in water (50 μL). The reaction vessel was degassed and heated at 40° C., for 18 hours. After cooling, water was added and the residue was extracted with ethyl acetate. The combined organic extracts were dried over magnesium sulfate, and concentrated in vacuo to yield a crude product, which was purified using preparative HPLC to afford 2-furan-2-yl-6-(3-phenyl-3-phenylamino-prop-1-ynyl)-[1,2,4]triazolo[1,5-a]pyrazin-8-ylamine. $^1$H NMR (300 MHz, Acetone-$d_6$) δ 8.20 (s, 1H), 7.79-7.71 (3H), 7.43-7.40(3H), 7.15-7.11(4H), 6.90-6.87(2H), 6.67-6.65 (2H), 5.70 (s, 1H), 2.55(s, 1H). MS: m/z 407 [M+1].

EXAMPLE 24

3-(8-Amino-2-furan-2-yl-[1,2,4]triazolo[1,5-a]pyrazin-6-ylethynyl)-3-hydroxy-piperidine-1-carboxylic acid tert-butyl ester Synthesis of the title compound is described in parts (a) and (b) below.

(a) 3-Ethynyl-3-hydroxy-piperidine-1-carboxylic acid tert-butyl ester

A solution of 3-oxo-piperidine-1-carboxylic acid tert-butyl ester (112 mg, 0.56 mmol) in THF (1 mL) was added dropwise to a solution of ethynylmagnesium bromide (0.5 M, 2.2 mL) in THF (1 mL) at 0° C. and the resulting mixture was stirred at 0° C. for 4 hours. The reaction was quenched with saturated aqueous $NH_4Cl$ and extracted with ethyl acetate. The combined organic extracts were washed with water, brine, dried over anhydrous magnesium sulfate, and concentrated to afford 3-ethynyl-3-hydroxy-piperidine-1-carboxylic acid tert-butyl ester (119 mg, 94%) as yellow oil. MS: m/z=226 amu ($M^+$+H).

(b) 3-(8-Amino-2-furan-2-yl-[1,2,4]triazolo[1,5-a] pyrazin-6-ylethynyl)-3-hydroxy-piperidine-1-carboxylic acid tert-butyl ester 3-(8-Amino-2-furan-2-yl-[1,2,4]triazolo[1,5-a]pyrazin-6-ylethynyl)-3-hydroxy-piperidine-1-carboxylic acid tert-butyl ester was prepared in an analogous manner as described in Example 3 (6% yield). $^1$H NMR (300 MHz, DMSO) δ 8.25 (br s, 1H), 7.92 (br s, 1H), 7.63 (s, 2H), 7.14 (br s, 1H), 6.72 (br s, 1H), 3.73-3.64 (m, 1H), 3.11 (m, 2H), 1.91 (m, 1H), 1.72-1.58 (m, 4H), 1.37 (s, 9 H). MS: m/z: 425 [M+H]$^+$.

EXAMPLE 25

6-{3-[(6-Chloro-2-fluoro-3-methyl-benzyl)-methyl-amino]-prop-1-ynyl}-2-furan-2-yl-[1,2,4]triazolo[1,5-a]pyrazin-8-ylamine Synthesis of the title compound is described in parts (a) and (b) below.

(a) (6-Chloro-2-fluoro-3-methyl-benzyl)-ethynyl-methyl-amine

To a solution of ethynyl-methylamine (98 uL, 1.16 mmol) and 6-chloro-2-fluoro-3-methyl-benzaldehyde (200 mg, 1.16 mmol) in CH$_2$Cl$_2$ (3 mL) was added sodium triacetoxyborohydride (369 mg, 1.74 mmol) and acetic acid (7 uL, 0.12 mmol). The reaction mixture was stirred at room temperature for 2 hours, quenched with saturated aqueous NaHCO$_3$, and extracted with ethyl acetate. The combined organic phases were washed with brine, dried over anhydrous magnesium sulfate, and concentrated to afford the title compound as yellow oil.

(b) 6-{3-[(6-Chloro-2-fluoro-3-methyl-benzyl)-methyl-amino]-prop-1-) ynyl}-2-furan-2-yl-[1,2,4]triazolo[1,5-a]pyrazin-8-ylamine 6-{3-[(6-Chloro-2-fluoro-3-methyl-benzyl)-methyl-amino]-prop-1-ynyl}-2-furan-2-yl-[1,2,4]triazolo[1,5-a]pyrazin-8-ylamine was prepared in an analogous manner as described in Example 3 (41% yield). $^1$H NMR (300 MHz, DMSO) δ 8.50 (br s, 1H), 7.92 (br s, 1H), 7.63 (s, 2H), 7.50-7.30 (m, 2H), 7.14 (br s, 1H), 6.72 (br s, 1H), 4.25 (br s, 3H), 2.70 (br s,2H), 2.25 (s, 3 H). MS: m/z: 426 [M+H]$^+$.

EXAMPLE 26

6-(3-Amino-prop-1-ynyl)-2-furan-2-yl-[1,2,4]triazolo[1,5-a]pyrazin-8-ylamine

To a solution of [3-(8-amino-2-furan-2-yl-[1,2,4]triazolo[1,5-a]pyrazin-6-yl)-prop-2-ynyl]-carbamic acid tert-butyl ester (100 mg, 0.28 mmol; see Ex. 41 below which was prepared according to Example 3 above) in CH$_2$Cl$_2$ (3 mL) was added trifluoroacetic acid (107 uL, 1.4 mmol). The reaction was stirred at room temperature for 2 hours. The solvent and trifluoroacetic acid was removed to yield 6-(3-amino-prop-1-ynyl)-2-furan-2-yl-[1,2,4]triazolo[1,5-a]pyrazin-8-ylamine as brown oil. The compound was used without further purification. MS: m/z=255 amu (M$^+$+H)

EXAMPLE 27

6-{3-[Bis-(2,4,6-trifluoro-benzyl)-amino]-prop-1-ynyl}-2-furan-2-yl-[1,2,4]triazolo[1,5-a]pyrazin-8-ylamine To a solution of 6-(3-amino-prop-1-ynyl)-2-furan-2-yl-[1,2,4]triazolo[1,5-a]pyrazin-8-ylamine (17.7 mg, 0.07 mmol, see Example 26 above) and 2,4,6-trifluoro-benzaldehyde (11 mg, 0.07 mmol) in CH$_2$Cl$_2$ (2 mL) was added sodium triacetoxyborohydride (22 mg, 0.10 mmol) and acetic acid (6 uL, 0.10 mmol). The reaction mixture was stirred at room temperature for 2 hours, quenched with saturated aqueous NaHCO$_3$, and extracted with ethyl acetate. The combined organic phases were washed with brine, dried over anhydrous magnesium sulfate, and concentrated to afford the title compound (4 mg, 9% yield). $^1$H NMR (300 MHz, DMSO) δδ 8.30 (br s, 1 H), 7.92 (br s, 1H), 7.63 (s, 2H), 7.10 (m, 5H), 6.72 (br s, 1H), 3.80 (s, 4 H), 3.50 (s, 2 H). MS: m/z: 543 [M+H]$^+$.

EXAMPLE 28

4-(8-Amino-2-furan-2-yl-[1,2,4]triazolo[1,5-a]pyrazin-6-yl)-3,6-dihydro-2H-pyridine-1-carboxylic acid tert-butyl ester A mixture of 6-bromo-2-furan-2-yl-[1,2,4]triazolo[1,5-a]pyrazin-8-ylamine (112 mg, 0.4 mmol; see Examples 1 and 2), 4-(4,4,5,5-tetramethyl-[1,3,2]dioxaborolan-2-yl)-3,6-dihydro-2H-pyridine-1-carboxylic acid tert-butyl ester (185 mg, 0.6 mmol; see Eastwood, P. *Tetrahedron Letters* 41:3705-3708 (2000) for its preparation), Pd(PPh$_3$)$_3$ (28 mg, 0.024 mmol), and aqueous Na$_2$CO$_3$ (2 M, 1 mL) in DMF (4 mL) was heated (at approximately 80° C.) for 16 hours. The reaction was filtered and then purified by HPLC (C18, H$_2$O:MeCN gradient) to afford 4-(8-amino-2-furan-2-yl-[1,2,4]triazolo[1,5-a]pyrazin-6-yl)-3,6-dihydro-2H-pyridine-1-carboxylic acid tert-butyl ester (72 mg, 47%). $^1$H NMR (400 MHz, DMSO-d$_6$) δ 1.43 (s, 9H), 2.47 (br. s, 2H), 3.54 (t, j=6.2 Hz, 2H), 4.05 (br. s, 2H), 6.7 (br. s, 1H), 6.7 (dd, J=3.3, 1.7 Hz, 1H), 7.12 (dd, J=3.5, 0.7 Hz, 1H), 7.91 (dd, J=1.7, 0.7 Hz, 1H), 8.18 (s, 1H). MS. m/z 383 [M+H]$^+$

EXAMPLE 29

4-(8-Amino-2-furan-2-yl-[1,2,4]triazolo[1,5-a]pyrazin-6-yl)-piperidine-1-carboxylic acid tert-butyl ester To a solution of 4-(8-amino-2-furan-2-yl-[1,2,4]triazolo[1,5-a]pyrazin-6-yl)-3,6-dihydro-2H-pyridine-1-carboxylic acid tert-butyl ester (50 mg, 0.13 mmol; see Example 28 above) in MeOH (1 mL) was added palladium (10 wt.% on activated carbon, 10 mg). The reaction mixture was stirred at room temperature under hydrogen atmosphere (1 atm) for overnight. The reaction mixture was filtered through Celite and the filtrate was concentrated to yield title compound (2.5 mg, 5%) as yellow solid. $^1$H NMR (300 MHz, DMSO) δ 8.01 (br s, 1H), 7.89 (s, 1H), 7.47 (s, 2H), 7.09 (br s, 1 H), 6.69 (br s, 1H), 4.06 (d, J=11.7 Hz, 2H), 2.80-2.63 (m, 3H), 1.84-1.80 (m, 2H), 1.69-1.64 (m, 2H), 1.41 (s, 9 H). MS m/z=385 amu (M$^+$+H).

EXAMPLE 30

2-Furan-2-yl-6-[1-(2,4,6-trifluoro-benzylamino)-cyclohexylethynyl]-[1,2,4]triazolo[1,5-a]pyrazin-8-ylamine A solution of 6-(1-amino-cyclohexylethynyl)-2-furan-2-yl-[1,2,4]triazolo[1,5-a]pyrazin-8-ylamine (45 mg, 0.14 mmol; see Ex. 61 below which was prepared according to Example 3 above) and 2,4,6-trifluorobenzaldehyde (19 mg, 0.12 mmol) in MeOH (1 mL) was stirred at room temperature for 3 hours. After that, sodium borohydride (7 mg, 0.18 mmol) was added to the solution. The reaction mixture was stirred at room temperature for 1 hour. The reaction mixture was filtered through a pad of silica gel, washed with ethyl acetate. The eluant was concentrated. The residue was isolated by reversed phased HPLC eluting with a water/acetonitrile gradient to yield 2-furan-2-yl-6-[1-(2,4,6-trifluoro-benzylamino)-cyclohexylethynyl]-[1,2,4]triazolo[1,5-a]pyrazin-8-ylamine (2 mg, 4%). $^1$H NMR (300 MHz, DMSO) δ 8.51 (br s, 1H), 7.89 (s, 1H), 7.67 (s,2H), 7.40 (br 2H), 7.09 (br s, 1H), 6.69 (br s, 1H), 4.35 (m, 2H), 2.35-2.20 (m, 2H), 1.84-1.60 (m, 8). MS: m/z 467 amu ($M^+$+H).

EXAMPLE 31

4-(8-Amino-2-furan-2-yl-[1,2,4]triazolo[1,5-a]pyrazin-6-yl)-1-(4-amino-phenyl)-2-methyl-but-3-yn-2-ol To a solution of 4-(8-amino-2-furan-2-yl-[1,2,4]triazolo[1,5-a]pyrazin-6-yl)-2-methyl-1-(4-nitro-phenyl)-but-3-yn-2-ol-(17.7 mg, 0.044 mmol;. see Ex. 72 below which was prepared according to Example 24 above) in DMF (3 mL) was added $SnCl_2.2H_2O$ (98 mg, 0.43 mmol) and the reaction was stirred at room temperature for overnight. The solvent was removed in vacuo and the residue was purified by reversed phase HPLC eluting with a water/acetonitrile gradient to yield the title compound (6.5 mg, 39%) as yellow solid. $^1$H NMR (300 MHz, DMSO) δ 8.25 (s, 1H), 7.93 (br s, 1 H), 7.60 (s, 2H), 7.33 (m, 2H), 7.14 (br s, 1H), 7.04 (m, 2H), 6.72 (br s, 1H), 2.82 (s, 2H), 1.38 (s,3 H). MS: m/z=375 amu ($M^+$+H).

EXAMPLE 32

4-(8-Amino-2-furan-2-yl-[1,2,4]triazolo[1,5-a]pyrazin-6-ylethynyl)-1-(2,4,6-trifluoro-benzyl)-piperidin-4-ol Synthesis of the title compound is described in parts (a) and (b) below.

(a) 4-(8-Amino-2-furan-2-yl-[1,2,4]triazolo[1,5-a]pyrazin-6-ylethynyl)-piperidin-4-ol To a solution of 4-(8-amino-2-furan-2-yl-[1,2,4]triazolo[1,5-a]pyrazin-6-ylethynyl)-4-hydroxy-piperidine-1-carboxylic acid tert-butyl ester (29 mg, 0.068 mmol; see Ex. 59 below which was prepared according to Example 24 above) in $CH_2Cl_2$ (2 mL) was added trifluoroacetic acid (200 uL). The reaction was stirred at room temperature for 2 hours. The solvent and trifluoroacetic acid was removed to yield 6-(3-amino-prop-1-ynyl)-2-furan-2-yl-[1,2,4]triazolo[1,5-a]pyrazin-8-ylamine. The compound was used without further purification.

(b) 4-(8-Amino-2-furan-2-yl-[1,2,4]triazolo[1,5-a]pyrazin-6-ylethynyl)-1-(2,4,6-trifluoro-benzyl)-piperidin-4-ol To a solution of 4-(8-amino-2-furan-2-yl-[1,2,4]triazolo[1,5-a]pyrazin-6-ylethynyl)-piperidin-4-ol (22 mg,0.068 mmol) and 2,4,6-trifluoro-benzaldehyde (11 mg, 0.068 mmol) in $CH_2Cl_2$ (2 mL) was added sodium triacetoxyborohydride (32 mg, 0.15 mmol) and acetic acid (6 uL, 0.10 mmol). The reaction mixture was stirred at room temperature for 2 hours. The reaction mixture was filtered through a pad of silica-gel, washed with ethyl acetate. The eluant was concentrated. The residue was isolated by reversed phased HPLC eluting with a water/acetonitrile gradient to yield 4-(8-amino-2-furan-2-yl-[1,2,4]triazolo[1,5-a]pyrazin-6-ylethynyl)-1-(2,4,6-trifluoro-benzyl)-piperidin-4-ol (1 mg, 3%). $^1$H NMR (300 MHz, DMSO): δ 7.92 (br s, 1H), 7.70 (m, 3H), 7.41 (s, 2H), 7.14 (s, 1H), 6.72 (s, 1H), 4.43 (s, 2H), 3.80 (m, 4H), 2.12-1.96 (m, 4 H). MS: m/z: 469 $[M+H]^+$.

EXAMPLE 33

S-2-(8-Amino-2-furan-2-yl-[1,2,4]triazolo[1,5-a]pyrazin-6-ylethynyl)-pyrrolidine-1-carboxylic acid tert-butyl ester The title compound was prepared in an analogous manner as described in Example 3 from S-2-ethynyl-pyrrolidine-1-carboxylic acid tert-butyl ester (for its preparation, see Trybulski, E. J et al., *J. Med. Chem.* 33:3190 (1990)).

EXAMPLE 34

R-2-(8-Amino-2-furan-2-yl-[1,2,4]triazolo[1,5-a]pyrazin-6-ylethynyl)-pyrrolide-1-carboxylic acid tert-butyl ester The title compound was prepared in an analogous-manner as described in Example 3 from R-2-ethynyl-pyrrolidine-1-carboxylic acid tert-butyl ester (for its preparation, see Trybulski, E. J et al., *J. Med. Chem.* 33:3190 (1990)).

EXAMPLE 35

S-trans-2-[2-(8-Amino-2-furan-2-yl-[1,2,4]triazolo[1,5-a]pyrazin-6-yl)-vinyl]-pyrrolidine-1-carboxylic acid tert-butyl ester and S-cis-2-[2-(8-Amino-2-furan-2-yl-[1,2,4]triazolo[1,5-a]pyrazin-6-yl)-vinyl]-pyrrolidine-1-carboxylic acid tert-butyl ester To a stirred solution of lithium aluminium hydride (42 mg, 1.1 mmol) in THF (2 mL) was added a solution of S-2-(8-amino-2-furan-2-yl-[1,2,4]triazolo[1,5-a]pyrazin-6-ylethynyl)-pyrrolidine-1-carboxylic acid tert-butyl ester (96 mg, 0.24 mmol; see Exsample 33 above) in THF (1 mL) at 0° C. The reaction was maintained at approximately 10° C. for 2 hours, and then quenched succesively with water (0.2 mL), 5 N NaOH (0.2 mL), and water again (0.6 mL) at 0° C. The insoluble material was removed by, filtration, washed with ethyl acetate, and the filtrate was concentrated in vacuo. The residue was subjected to flash chromatography using ethyl acetate/hexanes (40:60) as eluant to afford trans-compound (2 mg, 2%) as yellow oil and cis-compound (2 mg, 2%) as yellow oil.

S-trans-2-[2-(8-Amino-2-furan-2-yl-[1,2,4]triazolo[1,5-a]pyrazin-6-yl)-vinyl]-pyrrolidine-1-carboxylic acid tert-butyl ester: $^1$H NMR (300 MHz, DMSO) δ8.18 (s, 1 H), 7.90 (d, J=1.8 Hz, 1H), 7.42 (br s, 2H), 7.11 (d, J=3.3 Hz, 1H), 6.71 (dd, J=1.8, 3.3 Hz, 1H), 6.53 (dd, J=6.3, 15.3 Hz, 1 H); 6.30 (d, J=15.3 Hz, 1H), 4.37 (br s, 1H), 1.99 (m, 1H), 1.75-1.63 (m, 3H), 1.34 (s, 9H), 1.30-1.19 (m, 2 H). MS: m/z=397 amu ($M^+$+H).

S-cis-2-[2-(8-Amino-2-furan-2-yl-[1,2,4]triazolo[1,5-a]pyrazin-6-yl)-vinyl]-pyrrolidine-1-carboxylic acid tert-butyl ester: $^1$H NMR (300 MHz, DMSO) δ8.17 (s, 1 H), 7.91 (d, J=1.8 Hz, 1H), 7.41 (br s, 2H), 7.12 (d, J=3.3 Hz, 1H), 6.71 (dd, J=1.8, 3.3 Hz, 1H), 6.14 (dd, J=4.5, 8.7 Hz, 1H), 6.67 (d, J=8.7 Hz, 1H), 2.35 (m, 1 H), 1.83-1.63 (m, 4H), 1.38-1.19 (m, 12H). MS: m/z=397 amu (M$^+$+H)

| Example | Name | MS (m/z) [M + H]+ | Synthetic Method |
|---|---|---|---|
| Ex. 36 | 1-(8-Amino-2-furan-2-yl-[1,2,4]triazolo[1,5-a]pyrazin-6-ylethynyl)-cyclobutanol | 296 | Example 3 |
| Ex. 37 | 1-(8-Amino-2-furan-2-yl-[1,2,4]triazolo[1,5-a]pyrazin-6-ylethynyl)-cyclopentanol | 310 | Example 3 |
| Ex. 38 | 1-[8-Amino-2-(3-fluoro-phenyl)-[1,2,4]triazolo[1,5-a]pyrazin-6-ylethynyl]-cyclopentanol | 338 | Example 3 |
| Ex. 39 | 1-(8-Amino-2-furan-2-yl-[1,2,4]triazolo[1,5-a]pyrazin-6-ylethynyl)-cyclohexanol | 324 | Example 3 |
| Ex. 40 | 4-[8-Amino-2-(3-fluoro-phenyl)-[1,2,4]triazolo[1,5-a]pyrazin-6-yl]-2-phenyl-but-3-yn-2-ol | 374 | Example 3 |
| Ex. 41 | [3-(8-Amino-2-furan-2-yl-[1,2,4]triazolo[1,5-a]pyrazin-6-yl)-prop-2-ynyl]-carbamic acid tert-butyl ester | 355 | Example 3 |
| Ex. 42 | 2-Furan-2-yl-6-(3-methylamino-prop-1-ynyl)-[1,2,4]triazolo[1,5-a]pyrazin-8-ylamine | 269 | Example 3 |
| Ex. 43 | 2-(8-Amino-2-furan-2-yl-[1,2,4]triazolo[1,5-a]pyrazin-6-ylethynyl)-indan-2-ol | 358 | Example 24 |
| Ex. 44 | 1-(8-Amino-2-furan-2-yl-[1,2,4]triazolo[1,5-a]pyrazin-6-ylethynyl)-2,2,6-trimethyl-cyclohexanol | 366 | Example 3 |
| Ex. 45 | 1-(8-Amino-2-furan-2-yl-[1,2,4]triazolo[1,5-a]pyrazin-6-ylethynyl)-2-benzyl-cyclohexanol | 414 | Example 24 |
| Ex. 46 | 3-(8-Amino-2-furan-2-yl-[1,2,4]triazolo[1,5-a]pyrazin-6-yl)-prop-2-yn-1-ol | 256 | Example 3 |
| Ex. 47 | 6-(3-Cyclohexyl-prop-1-ynyl)-2-furan-2-yl-[1,2,4]triazolo[1,5-a]pyrazin-8-ylamine | 322 | Example 3 |
| Ex. 48 | 6-(3-Cyclopentyl-prop-1-ynyl)-2-furan-2-yl-[1,2,4]triazolo[1,5-a]pyrazin-8-ylamine | 308 | Example 3 |
| Ex. 49 | 6-[3-(Benzyl-methyl-amino)-prop-1-ynyl]-2-furan-2-yl-[1,2,4]triazolo[1,5-a]pyrazin-8-ylamine | 359 | Example 3 |
| Ex. 50 | 6-[3-(6-Chloro-2-fluoro-3-methyl-benzylamino)-prop-1-ynyl]-2-furan-2-yl-[1,2,4]triazolo[1,5-a]pyrazin-8-ylamine | 412 | Example 27 |
| Ex. 51 | N-[3-(8-Amino-2-furan-2-yl-[1,2,4]triazolo[1,5-a]pyrazin-6-yl)-prop-2-ynyl]-2,4,6-trifluoro-benzamide | 413 | Example 20 |
| Ex. 52 | N-[3-(8-Amino-2-furan-2-yl-[1,2,4]triazolo[1,5-a]pyrazin-6-yl)-prop-2-ynyl]-2,4-difluoro-benzamide | 395 | Example 20 |
| Ex. 53 | N-[3-(8-Amino-2-furan-2-yl-[1,2,4]triazolo[1,5-a]pyrazin-6-yl)-prop-2-ynyl]-2-pyridin-4-yl-acetamide | 374 | Example 20 |
| Ex. 54 | 3,5-Dimethyl-isoxazole-4-carboxylic acid [3-(8-amino-2-furan-2-yl-[1,2,4]triazolo[1,5-a]pyrazin-6-yl)-prop-2-ynyl]-amide | 378 | Example 20 |
| Ex. 55 | 5-Methyl-isoxazole-3-carboxylic acid [3-(8-amino-2-furan-2-yl-[1,2,4]triazolo[1,5-a]pyrazin-6-yl)-prop-2-ynyl]-amide | 364 | Example 20 |
| Ex. 56 | 2,5-Dimethyl-2H-pyrazole-3-carboxylic acid [3-(8-amino-2-furan-2-yl-[1,2,4]triazolo[1,5-a]pyrazin-6-yl)-prop-2-ynyl]-amide | 377 | Example 20 |
| Ex. 57 | 2,4-Dimethyl-thiazole-5-carboxylic acid [3-(8-amino-2-furan-2-yl-[1,2,4]triazolo[1,5-a]pyrazin-6-yl)-prop-2-ynyl]-amide | 394 | Example 20 |
| Ex. 58 | 4-Methyl-2-pyrazin-2-yl-thiazole-5-carboxylic acid [3-(8-Amino-2-furan-2-yl-[1,2,4]triazolo[1,5-a]pyrazin-6-yl)-prop-2-ynyl]-amide | 458 | Example 20 |
| Ex. 59 | 4-(8-Amino-2-furan-2-yl-[1,2,4]triazolo[1,5-a]pyrazin-6-ylethynyl)-4-hydroxy-piperidine-1-carboxylic acid tert-butyl ester | 425 | Example 24 |
| Ex. 60 | 4-(8-Amino-2-furan-2-yl-[1,2,4]triazolo[1,5-a]pyrazin-6-ylethynyl)-1-isopropyl-piperidin-4-ol | 367 | Example 32 |
| Ex. 61 | 6-(1-Amino-cyclohexylethynyl)-2-furan-2-yl-[1,2,4]triazolo[1,5-a]pyrazin-8-ylamine | 323 | Example 3 |
| Ex. 62 | 2-Furan-2-yl-6-(4-trifluoromethyl-phenylethynyl)-[1,2,4]triazolo[1,5-a]pyrazin-8-ylamine | 370 | Example 3 |
| Ex. 63 | 2-Furan-2-yl-6-(4-pentyl-phenylethynyl)-[1,2,4]triazolo[1,5-a]pyrazin-8-ylamine | 372 | Example 3 |
| Ex. 64 | 6-(2,4-Difluoro-phenylethynyl)-2-furan-2-yl-[1,2,4]triazolo[1,5-a]pyrazin-8-ylamine | 338 | Example 3 |
| Ex. 65 | 2-Furan-2-yl-6-pyridin-2-ylethynyl-[1,2,4]triazolo[1,5-a]pyrazin-8-ylamine | 303 | Example 3 |
| Ex. 66 | 4-(8-Amino-2-furan-2-yl-[1,2,4]triazolo[1,5-a]pyrazin-6-yl)-1-(3-trifluoromethyl-phenoxy)-but-3-yn-2-ol | 430 | Example 3 |
| Ex. 67 | 4-(8-Amino-2-furan-2-yl-[1,2,4]triazolo[1,5-a]pyrazin-6-yl)-2-methyl-1-phenoxy-but-3-yn-2-ol | 376 | Example 24 |

-continued

| Example | Name | MS (m/z) [M + H]+ | Synthetic Method |
|---|---|---|---|
| Ex. 68 | 1-(8-Amino-2-furan-2-yl-[1,2,4]triazolo[1,5-a]pyrazin-6-yl)-5-phenyl-pent-1-yn-3-ol | 360 | Example 24 |
| Ex. 69 | 1-(8-Amino-2-furan-2-yl-[1,2,4]triazolo[1,5-a]pyrazin-6-yl)-3-methyl-5-phenyl-pent-1-yn-3-ol | 374 | Example 24 |
| Ex. 70 | 4-(8-Amino-2-furan-2-yl-[1,2,4]triazolo[1,5-a]pyrazin-6-yl)-1-furan-2-yl-2-methyl-but-3-yn-2-ol | 350 | Example 24 |
| Ex. 71 | 4-(8-Amino-2-furan-2-yl-[1,2,4]triazolo[1,5-a]pyrazin-6-yl)-1-(3-fluoro-phenyl)-2-methyl-but-3-yn-2-ol | 378 | Example 24 |
| Ex. 72 | 4-(8-Amino-2-furan-2-yl-[1,2,4]triazolo[1,5-a]pyrazin-6-yl)-2-methyl-1-(4-nitro-phenyl)-but-3-yn-2-ol | 405 | Example 24 |
| Ex. 73 | 4-(8-Amino-2-furan-2-yl-[1,2,4]triazolo[1,5-a]pyrazin-6-yl)-2-methyl-1-pyridin-4-yl-but-3-yn-2-ol | 361 | Example 24 |
| Ex. 74 | 1-(8-Amino-2-furan-2-yl-[1,2,4]triazolo[1,5-a]pyrazin-6-yl)-3-methyl-non-1-yn-3-ol | 354 | Example 24 |
| Ex. 75 | 1-(8-Amino-2-furan-2-yl-[1,2,4]triazolo[1,5-a]pyrazin-6-yl)-3-(2-fluoro-3-trifluoromethyl-phenyl)-pent-1-yn-3-ol | 446 | Example 24 |
| Ex. 76 | 4-(8-Amino-2-furan-2-yl-[1,2,4]triazolo[1,5-a]pyrazin-6-yl)-2-(4-dimethylamino-phenyl)-1,1,1-trifluoro-but-3-yn-2-ol | 443 | Example 3 |
| Ex. 77 | 6-(3-tert-Butoxy-but-1-ynyl)-2-furan-2-yl-[1,2,4]triazolo[1,5-a]pyrazin-8-ylamine | 326 | Example 22 |
| Ex. 78 | 2-Furan-2-yl-6-[3-(pyridin-3-yloxy)-prop-1-ynyl]-[1,2,4]triazolo[1,5-a]pyrazin-8-ylamine | 333 | Example 22 |
| Ex. 79 | 2-Furan-2-yl-6-[3-(1-methyl-5-trifluoromethyl-1H-pyrazol-3-yloxy)-prop-1-ynyl]-[1,2,4]triazolo[1,5-a]pyrazin-8-ylamine | 404 | Example 22 |
| Ex. 80 | 6-{3-[4-(3,5-Dichloro-pyridin-4-ylmethyl)-phenoxy]-prop-1-ynyl}-2-furan-2-yl-[1,2,4]triazolo[1,5-a]pyrazin-8-ylamine | 492 | Example 22 |
| Ex. 81 | 2-Furan-2-yl-6-[3-(4-imidazol-1-yl-phenoxy)-prop-1-ynyl]-[1,2,4]triazolo[1,5-a]pyrazin-8-ylamine | 398 | Example 22 |
| Ex. 82 | 6-[3-(3-Dimethylamino-phenoxy)-prop-1-ynyl]-2-furan-2-yl-[1,2,4]triazolo[1,5-a]pyrazin-8-ylamine | 375 | Example 22 |
| Ex. 83 | 6-[3-(3-Chloro-4-fluoro-phenoxy)-prop-1-ynyl]-2-furan-2-yl-[1,2,4]triazolo[1,5-a]pyrazin-8-ylamine | 385 | Example 22 |
| Ex. 84 | N-[3-(8-Amino-2-furan-2-yl-[1,2,4]triazolo[1,5-a]pyrazin-6-yl)-prop-2-ynyl]-isonicotinamide | 360 | Example 20 |
| Ex. 85 | 6-(8-Amino-2-furan-2-yl-[1,2,4]triazolo[1,5-a]pyrazin-6-yl)-hex-5-ynenitrile | 293 | Example 3 |
| Ex. 86 | 4-(8-Amino-2-furan-2-yl-[1,2,4]triazolo[1,5-a]pyrazin-6-yl)-2-phenyl-but-3-yn-2-ol | 346 | Example 3 |
| Ex. 87 | 4-(8-Amino-2-furan-2-yl-[1,2,4]triazolo[1,5-a]pyrazin-6-yl)-2-pyridin-4-yl-but-3-yn-2-ol | 347 | Example 3 |
| Ex. 88 | 4-(8-Amino-2-furan-2-yl-[1,2,4]triazolo[1,5-a]pyrazin-6-yl)-2-(3-trifluoromethoxy-phenyl)-but-3-yn-2-ol | 430 | Example 24 |
| Ex. 89 | 4-(8-Amino-2-furan-2-yl-[1,2,4]triazolo[1,5-a]pyrazin-6-yl)-2-(2-fluoro-3-trifluoromethyl-phenyl)-but-3-yn-2-ol | 432 | Example 24 |
| Ex. 90 | 4-[3-(8-Amino-2-furan-2-yl-[1,2,4]triazolo[1,5-a]pyrazin-6-yl)-1-hydroxy-1-methyl-prop-2-ynyl]-phenol | 362 | Example 3 |
| Ex. 91 | 4-(8-Amino-2-furan-2-yl-[1,2,4]triazolo[1,5-a]pyrazin-6-yl)-2-naphthalen-2-yl-but-3-yn-2-ol | 396 | Example 24 |
| Ex. 92 | 4-(8-Amino-2-furan-2-yl-[1,2,4]triazolo[1,5-a]pyrazin-6-yl)-2-benzo[b]thiophen-3-yl-but-3-yn-2-ol | 402 | Example 24 |
| Ex. 93 | 4-(8-Amino-2-furan-2-yl-[1,2,4]triazolo[1,5-a]pyrazin-6-yl)-2-biphenyl-4-yl-but-3-yn-2-ol | 422 | Example 24 |
| Ex. 94 | 4-(8-Amino-2-furan-2-yl-[1,2,4]triazolo[1,5-a]pyrazin-6-yl)-2-(4-imidazol-1-yl-phenyl)-but-3-yn-2-ol | 412 | Example 3 |
| Ex. 95 | 2-[6-(8-Amino-2-furan-2-yl-[1,2,4]triazolo[1,5-a]pyrazin-6-yl)-hex-5-ynyl]-isoindole-1,3-dione | 427 | Example 3 |
| Ex. 96 | 2-Furan-2-yl-6-[3-(tetrahydro-pyran-2-yloxy)-prop-1-ynyl]-[1,2,4]triazolo[1,5-a]pyrazin-8-ylamine | 340 | Example 3 |
| Ex. 97 | 6-{3-[4-(2,4-Difluoro-phenyl)-piperazin-1-yl]-prop-1-ynyl}-2-furan-2-yl-[1,2,4]triazolo[1,5-a]pyrazin-8-ylamine | 436 | Example 12 |
| Ex. 98 | 2-Furan-2-yl-6-{3-[4-(2,4,6-trifluoro-phenyl)-piperazin-1-yl]-prop-1-ynyl}-[1,2,4]triazolo[1,5-a]pyrazin-8-ylamine | 454 | Example 12 |
| Ex. 99 | 2-Furan-2-yl-6-(3-piperazin-1-yl-propyl)-[1,2,4]triazolo[1,5-a]pyrazin-8-ylamine | 328 | Example 26 |
| Ex. 100 | 6-{3-[4-(2,4-Difluoro-phenyl)-piperazin-1-yl]-propyl}-2-furan-2-yl-[1,2,4]triazolo[1,5-a]pyrazin-8-ylamine | 440 | Example 13 |
| Ex. 101 | 1-(8-Amino-2-furan-2-yl-[1,2,4]triazolo[1,5-a]pyrazin-6-yl)-3-methyl-pent-1-yn-3-ol | 298 | Example 3 |

-continued

| Example | Name | MS (m/z) [M + H]+ | Synthetic Method |
|---|---|---|---|
| Ex. 102 | 1-(8-Amino-2-furan-2-yl-[1,2,4]triazolo[1,5-a]pyrazin-6-yl)-3-isopropyl-4-methyl-pent-1-yn-3-ol | 340 | Example 3 |
| Ex. 103 | 1-(8-Amino-2-furan-2-yl-[1,2,4]triazolo[1,5-a]pyrazin-6-yl)-3-ethyl-pent-1-yn-3-ol | 312 | Example 3 |
| Ex. 104 | 1-(8-Amino-2-furan-2-yl-[1,2,4]triazolo[1,5-a]pyrazin-6-yl)-3,6-dimethyl-hept-1-yn-3-ol | 340 | Example 3 |
| Ex. 105 | 1-(8-Amino-2-furan-2-yl-[1,2,4]triazolo[1,5-a]pyrazin-6-yl)-3,5-dimethyl-hept-1-yn-3-ol | 326 | Example 3 |
| Ex. 106 | 1-(8-Amino-2-furan-2-yl-[1,2,4]triazolo[1,5-a]pyrazin-6-yl)-3,4,4-trimethyl-pent-1-yn-3-ol | 326 | Example 3 |
| Ex. 107 | 4-(8-Amino-2-furan-2-yl-[1,2,4]triazolo[1,5-a]pyrazin-6-yl)-1,1,1-trifluoro-2-phenyl-but-3-yn-2-ol | 400 | Example 3 |
| Ex. 108 | 3-(8-Amino-2-furan-2-yl-[1,2,4]triazolo[1,5-a]pyrazin-6-yl)-1,1-diphenyl-prop-2-yn-1-ol | 408 | Example 3 |
| Ex. 109 | 3-(8-Amino-2-furan-2-yl-[1,2,4]triazolo[1,5-a]pyrazin-6-yl)-1-phenyl-prop-2-yn-1-ol | 332 | Example 3 |
| Ex. 110 | 3-(8-Amino-2-furan-2-yl-[1,2,4]triazolo[1,5-a]pyrazin-6-yl)-1-[4-(4-methyl-piperazin-1-yl)-phenyl]-prop-2-yn-1-ol | 430 | Example 3 |
| Ex. 111 | 3-(8-Amino-2-furan-2-yl-[1,2,4]triazolo[1,5-a]pyrazin-6-yl)-1-benzo[1,3]dioxol-4-yl-prop-2-yn-1-ol | 376 | Example 24 |
| Ex. 112 | 3-(8-Amino-2-furan-2-yl-[1,2,4]triazolo[1,5-a]pyrazin-6-yl)-1-benzo[b]thiophen-2-yl-prop-2-yn-1-ol | 388 | Example 24 |
| Ex. 113 | 2-Furan-2-yl-6-[1-(5-methyl-isoxazol-3-ylmethyl)-1,2,3,6-tetrahydro-pyridin-4-yl]-[1,2,4]triazolo[1,5-a]pyrazin-8-ylamine | 378 | Example 32 |
| Ex. 114 | 6-[1-(5-Chloro-1-methyl-3-trifluoromethyl-1H-pyrazol-4-ylmethyl)-1,2,3,6-tetrahydro-pyridin-4-yl]-2-furan-2-yl-[1,2,4]triazolo[1,5-a]pyrazin-8-ylamine | 480 | Example 32 |
| Ex. 115 | 6-[1-(5-Chloro-1-methyl-3-trifluoromethyl-1H-pyrazol-4-ylmethyl)-piperidin-4-yl]-2-furan-2-yl-[1,2,4]triazola[1,5-a]pyrazin-8-ylamine | 482 | Example 32 |
| Ex. 116 | 2-Furan-2-yl-6-[1-(2,4,6-trifluoro-benzyl)-1,2,3,6-tetrahydro-pyridin-4-yl]-[1,2,4]triazolo[1,5-a]pyrazin-8-ylamine | 427 | Example 32 |
| Ex. 117 | 2-Furan-2-yl-6-[1-(2,4,6-trifluoro-benzyl)-piperidin-4-yl]-[1,2,4]triazolo[1,5-a]pyrazin-8-ylamine | 429 | Example 32 |
| Ex. 118 | 3-(8-Amino-2-furan-2-yl-[1,2,4]triazolo[1,5-a]pyrazin-6-ylethynyl)-1-(2,4,6-trifluoro-benzyl)-piperidin-3-ol | 469 | Example 32 |
| Ex. 119 | 6-[1-(6-Chloro-2-fluoro-3-methyl-benzyl)-1,2,3,6-tetrahydro-pyridin-4-yl]-2-furan-2-yl-[1,2,4]triazolo[1,5-a]pyrazin-8-ylamine | 440 | Example 32 |
| Ex. 120 | 2-Furan-2-yl-6-(1-quinolin-4-ylmethyl-1,2,3,6-tetrahydro-pyridin-4-yl)-[1,2,4]triazolo[1,5-a]pyrazin-8-ylamine | 424 | Example 32 |
| Ex. 121 | S-2-Furan-2-yl-6-[1-(2,4,6-trifluoro-benzyl)-2-ylethynyl]-[1,2,4]triazolo[1,5-a]pyrazin-8-ylamine | 439 | Example 32 |
| Ex. 122 | R-2-Furan-2-yl-6-[1-(2,4,6-trifluoro-benzyl)-pyrrolidin-2-ylethynyl]-[1,2,4]triazolo[1,5-a]pyrazin-8-ylamine | 439 | Example 32 |
| Ex. 123 | S-6-[1-(5-Chloro-furan-2-ylmethyl)-pyrrolidin-2-ylethynyl]-2-furan-2-yl-[1,2,4]triazolo[1,5-a]pyrazin-8-ylamine | 410 | Example 32 |
| Ex. 124 | R-6-[1-(5-Chloro-furan-2-ylmethyl)-pyrrolidin-2-ylethynyl]-2-furan-2-yl-[1,2,4]triazolo[1,5-a]pyrazin-8-ylamine | 410 | Example 32 |
| Ex. 125 | S-2-Furan-2-yl-6-(1-quinolin-3-ylmethyl-pyrrolidin-2-ylethynyl)-[1,2,4]triazolo[1,5-a]pyrazin-8-ylamine | 436 | Example 32 |
| Ex. 126 | R-2-Furan-2-yl-6-(1-quinolin-3-ylmethyl-pyrrolidin-2-ylethynyl)-[1,2,4]triazolo[1,5-a]pyrazin-8-ylamine | 436 | Example 32 |
| Ex. 127 | S-6-[1-(4-Bromo-1-methyl-1H-pyrazol-3-ylmethyl)-pyrrolidin-2-ylethynyl]-2-furan-2-yl-[1,2,4]triazolo[1,5-a]pyrazin-8-ylamine | 468 | Example 32 |
| Ex. 128 | R-6-[1-(4-Bromo-1-methyl-1H-pyrazol-3-ylmethyl)-pyrrolidin-2-ylethynyl]-2-furan-2-yl-[1,2,4]triazolo[1,5-a]pyrazin-8-ylamine | 468 | Example 32 |
| Ex. 129 | S-6-[1-(3,5-Dimethyl-isoxazol-4-ylmethyl)-pyrrolidin-2-ylethynyl]-2-furan-2-yl-[1,2,4]triazolo[1,5-a]pyrazin-8-ylamine | 404 | Example 32 |
| Ex. 130 | R-6-[1-(3,5-Dimethyl-isoxazol-4-ylmethyl)-pyrrolidin-2-ylethynyl]-2-furan-2-yl-[1,2,4]triazolo[1,5-a]pyrazin-8-ylamine | 404 | Example 32 |
| Ex. 131 | S-6-[1-(5-Chloro-1-methyl-3-trifluoromethyl-1H-pyrazol-4-ylmethyl)-pyrrolidin-2-ylethynyl]-2-furan-2-yl-[1,2,4]triazolo[1,5-a]pyrazin-8-ylamine | 492 | Example 32 |

-continued

| Example | Name | MS (m/z) [M + H]+ | Synthetic Method |
|---|---|---|---|
| Ex. 132 | S-2-Furan-2-yl-6-[1-(5-methyl-isoxazol-3-ylmethyl)-pyrrolidin-2-ylethynyl]-[1,2,4]triazolo[1,5-a]pyrazin-8-ylamine | 390 | Example 32 |
| Ex. 133 | S-2-[2-(8-Amino-2-furan-2-yl-[1,2,4]triazolo[1,5-a]pyrazin-6-yl)-ethyl]-pyrrolidine-1-carboxylic acid tert-butyl ester | 399 | Example 13 |
| Ex. 134 | R-2-[2-(8-Amino-2-furan-2-yl-[1,2,4]triazolo[1,5-a]pyrazin-6-yl)-ethyl]-pyrrolidine-1-carboxylic acid tert-butyl ester | 399 | Example 13 |
| Ex. 135 | R-2-Furan-2-yl-6-{2-[1-(2,4,6-trifluoro-benzyl)-pyrrolidin-2-yl]-ethyl}-[1,2,4]triazolo[1,5-a]pyrazin-8-ylamine | 443 | Example 32 |
| Ex. 136 | R-6-{2-[1-(4-Bromo-1-methyl-1H-pyrazol-3-ylmethyl)-pyrrolidin-2-yl]-ethyl}-2-furan-2-yl-[1,2,4]triazolo[1,5-a]pyrazin-8-ylamine | 472 | Example 32 |
| Ex. 137 | R-6-{2-[1-(5-Chloro-furan-2-ylmethyl)-pyrrolidin-2-yl]-ethyl}-2-furan-2-yl-[1,2,4]triazolo[1,5-a]pyrazin-8-ylamine | 414 | Example 32 |
| Ex. 138 | S-6-{2-[1-(5-Chloro-furan-2-ylmethyl)-pyrrolidin-2-yl]-ethyl}-2-furan-2-yl-[1,2,4]triazolo[1,5-a]pyrazin-8-ylamine | 414 | Example 32 |
| Ex. 139 | R-6-{2-[1-(3,5-Dimethyl-isoxazol-4-ylmethyl)-pyrrolidin-2-yl]-ethyl}-2-furan-2-yl-[1,2,4]triazolo[1,5-a]pyrazin-8-ylamine | 408 | Example 32 |
| Ex. 140 | 2-Furan-2-yl-6-hex-1-enyl-[1,2,4]triazolo[1,5-a]pyrazin-8-ylamine | 284 | Example 4 |
| Ex. 141 | 3-(8-Amino-2-furan-2-yl-[1,2,4]triazolo[1,5-a]pyrazin-6-yl)-benzoic acid ethyl ester | 350 | Example 4 |
| Ex. 142 | 3-(8-Amino-2-furan-2-yl-[1,2,4]triazolo[1,5-a]pyrazin-6-yl)-benzamide | 321 | Example 6 |
| Ex. 143 | 3-(8-Amino-2-furan-2-yl-[1,2,4]triazolo[1,5-a]pyrazin-6-yl)-N-isopropyl-benzamide | 363 | Example 6 |
| Ex. 144 | 3-(8-Amino-2-furan-2-yl-[1,2,4]triazolo[1,5-a]pyrazin-6-yl)-N-butyl-benzamide | 377 | Example 6 |
| Ex. 145 | 3-(8-Amino-2-furan-2-yl-[1,2,4]triazolo[1,5-a]pyrazin-6-yl)-N-[2-(4-hydroxy-phenyl)-ethyl]-benzamide | 441 | Example 6 |
| Ex. 146 | 3-(8-Amino-2-furan-2-yl-[1,2,4]triazolo[1,5-a]pyrazin-6-yl)-N,N-dimethyl-benzamide | 349 | Example 6 |
| Ex. 147 | 3-(8-Amino-2-furan-2-yl-[1,2,4]triazolo[1,5-a]pyrazin-6-yl)-N,N-diethyl-benzamide | 77 | Example 6 |
| Ex. 148 | [3-(8-Amino-2-furan-2-yl-[1,2,4]triazolo[1,5-a]pyrazin-6-yl)-phenyl]-pyrrolidin-1-yl-methanone | 375 | Example 6 |
| Ex. 149 | [3-(8-Amino-2-furan-2-yl-[1,2,4]triazolo[1,5-a]pyrazin-6-yl)-phenyl]-morpholin-4-yl-methanone | 391 | Example 6 |
| Ex. 150 | 1-[3-(8-Amino-2-furan-2-yl-[1,2,4]triazolo[1,5-a]pyrazin-6-yl)-benzoyl]-piperidine-3-carboxylic acid ethyl ester | 461 | Example 6 |
| Ex. 151 | [3-(8-Amino-2-furan-2-yl-[1,2,4]triazolo[1,5-a]pyrazin-6-yl)-phenyl]-(4-benzyl-piperazin-1-yl)-methanone | 481 | Example 6 |
| Ex. 152 | [3-(8-Amino-2-furan-2-yl-[1,2,4]triazolo[1,5-a]pyrazin-6-yl)-phenyl]-(4-pyridin-4-yl-piperazin-1-yl)-methanone | 468 | Example 6 |
| Ex. 153 | [3-(8-Amino-2-furan-2-yl-[1,2,4]triazolo[1,5-a]pyrazin-6-yl)-phenyl]-(4-pyridin-2-yl-piperazin-1-yl)-methanone | 468 | Example 6 |
| Ex. 154 | [4-(8-Amino-2-furan-2-yl-[1,2,4]triazolo[1,5-a]pyrazin-6-yl)-phenyl]-(4-pyridin-2-yl-piperazin-1-yl)-methanone | 468 | Example 6 |
| Ex. 155 | [4-(8-Amino-2-furan-2-yl-[1,2,4]triazolo[1,5-a]pyrazin-6-yl)-phenyl]-(4-pyridin-4-yl-piperazin-1-yl)-methanone | 468 | Example 6 |
| Ex. 156 | 4-(8-Amino-2-furan-2-yl-[1,2,4]triazolo[1,5-a]pyrazin-6-yl)-N-isopropyl-benzamide | 363 | Example 6 |
| Ex. 157 | 4-(8-Amino-2-furan-2-yl-[1,2,4]triazolo[1,5-a]pyrazin-6-yl)-N-[2-(4-hydroxy-phenyl)-ethyl]-benzamide | 441 | Example 6 |
| Ex. 158 | 4-(8-Amino-2-furan-2-yl-[1,2,4]triazolo[1,5-a]pyrazin-6-yl)-N-(3-imidazol-1-yl-propyl)-benzamide | 429 | Example 6 |
| Ex. 159 | 4-(8-Amino-2-furan-2-yl-[1,2,4]triazolo[1,5-a]pyrazin-6-yl)-N-butyl-benzamide | 377 | Example 6 |
| Ex. 160 | 1-[4-(8-Amino-2-furan-2-yl-[1,2,4]triazolo[1,5-a]pyrazin-6-yl)-benzoyl]-piperidine-3-carboxylic acid ethyl ester | 461 | Example 6 |
| Ex. 161 | [4-(8-Amino-2-furan-2-yl-[1,2,4]triazolo[1,5-a]pyrazin-6-yl)-phenyl]-morpholin-4-yl-methanone | 391 | Example 6 |

-continued

| Example | Name | MS (m/z) [M + H]+ | Synthetic Method |
|---|---|---|---|
| Ex. 162 | [4-(8-Amino-2-furan-2-yl-[1,2,4]triazolo[1,5-a]pyrazin-6-yl)-phenyl]-pyrrolidin-1-yl-methanone | 375 | Example 6 |
| Ex. 163 | [4-(8-Amino-2-furan-2-yl-[1,2,4]triazolo[1,5-a]pyrazin-6-yl)-phenyl]-piperidin-1-yl-methanone | 389 | Example 6 |
| Ex. 164 | 2-Furan-2-yl-6-pyridin-3-yl-[1,2,4]triazolo[1,5-a]pyrazin-8-ylamine | 279 | Example 4 |
| Ex. 165 | 2-Furan-2-yl-6-m-tolyl-[1,2,4]triazolo[1,5-a]pyrazin-8-ylamine | 292 | Example 4 |
| Ex. 166 | 6-(3,4-Dichloro-phenyl)-2-furan-2-yl-[1,2,4]triazolo[1,5-a]pyrazin-8-ylamine | 347 | Example 4 |
| Ex. 167 | 6-(3,5-Bis-trifluoromethyl-phenyl)-2-furan-2-yl-[1,2,4]triazolo[1,5-a]pyrazin-8-ylamine | 414 | Example 4 |
| Ex. 168 | 2-Furan-2-yl-6-(4-methylsulfanyl-phenyl)-[1,2,4]triazolo[1,5-a]pyrazin-8-ylamine | 324 | Example 4 |
| Ex. 169 | 6-(3-Amino-phenyl)-2-furan-2-yl-[1,2,4]triazolo[1,5-a]pyrazin-8-ylamine | 293 | Example 4 |
| Ex. 170 | 2,6-Di-furan-2-yl-[1,2,4]triazolo[1,5-a]pyrazin-8-ylamine | 268 | Example 4 |
| Ex. 171 | 6-(4-Dimethylamino-phenyl)-2-furan-2-yl-[1,2,4]triazolo[1,5-a]pyrazin-8-ylamine | 321 | Example 4 |
| Ex. 172 | 2-Furan-2-yl-6-naphthalen-1-yl-[1,2,4]triazolo[1,5-a]pyrazin-8-ylamine | 328 | Example 4 |
| Ex. 173 | [3-(8-Amino-2-furan-2-yl-[1,2,4]triazolo[1,5-a]pyrazin-6-yl)-phenyl]-methanol | 308 | Example 4 |
| Ex. 174 | 3-[3-(8-Amino-2-furan-2-yl-[1,2,4]triazolo[1,5-a]pyrazin-6-yl)-phenyl]-acrylic acid | 348 | Example 4 |
| Ex. 175 | 6-(3-Benzyloxy-phenyl)-2-furan-2-yl-[1,2,4]triazolo[1,5-a]pyrazin-8-ylamine | 384 | Example 4 |
| Ex. 176 | 2-Furan-2-yl-6-(2,4,6-trimethyl-phenyl)-[1,2,4]triazolo[1,5-a]pyrazin-8-ylamine | 320 | Example 4 |
| Ex. 177 | 3-(8-Amino-2-furan-2-yl-[1,2,4]triazolo[1,5-a]pyrazin-6-yl)-benzaldehyde | 306 | Example 4 |
| Ex. 178 | 3-[3-(8-Amino-2-furan-2-yl-[1,2,4]triazolo[1,5-a]pyrazin-6-yl)-phenyl]-acrylic acid ethyl ester | 376 | Example 4 |
| Ex. 179 | [4-(8-Amino-2-furan-2-yl-[1,2,4]triazolo[1,5-a]pyrazin-6-yl)-phenyl]-methanol | 308 | Example 4 |
| Ex. 180 | 2-Furan-2-yl-6-(3-{[(pyridin-2-ylmethyl)-amino]-methyl}-phenyl)-[1,2,4]triazolo[1,5-a]pyrazin-8-ylamine | 398 | Example 4 |
| Ex. 181 | 4-(8-Amino-2-furan-2-yl-[1,2,4]triazolo[1,5-a]pyrazin-6-yl)-benzaldehyde | 306 | Example 4 |
| Ex. 182 | 2-Furan-2-yl-6-(4-{[(pyridin-2-ylmethyl)-amino]-methyl}-phenyl)-[1,2,4]triazolo[1,5-a]pyrazin-8-ylamine | 398 | Example 4 |
| Ex. 183 | 2-Furan-2-yl-6-quinolin-8-yl-[1,2,4]triazolo[1,5-a]pyrazin-8-ylamine | 329 | Example 4 |
| Ex. 184 | 6-(2-Fluoro-biphenyl-4-yl)-2-furan-2-yl-[1,2,4]triazolo[1,5-a]pyrazin-8-ylamine | 372 | Example 4 |
| Ex. 185 | 6-(3-Aminomethyl-phenyl)-2-furan-2-yl-[1,2,4]triazolo[1,5-a]pyrazin-8-ylamine | 307 | Example 4 |
| Ex. 186 | 2-Furan-2-yl-6-furan-3-yl-[1,2,4]triazolo[1,5-a]pyrazin-8-ylamine | 268 | Example 4 |
| Ex. 187 | 3-(8-Amino-2-furan-2-yl-[1,2,4]triazolo[1,5-a]pyrazin-6-yl)-benzonitrile | 303 | Example 4 |
| Ex. 188 | 2-Furan-2-yl-6-(1H-indol-6-yl)-[1,2,4]triazolo[1,5-a]pyrazin-8-ylamine | 317 | Example 4 |
| Ex. 189 | 6-Benzofuran-2-yl-2-furan-2-yl-[1,2,4]triazolo[1,5-a]pyrazin-8-ylamine | 318 | Example 4 |
| Ex. 190 | 2-Furan-2-yl-6-(3-isopropyl-phenyl)-[1,2,4]triazolo[1,5-a]pyrazin-8-ylamine | 320 | Example 4 |
| Ex. 191 | 6-(2,4-Dimethoxy-pyrimidin-5-yl)-2-furan-2-yl-[1,2,4]triazolo[1,5-a]pyrazin-8-ylamine | 309 | Example 4 |
| Ex. 192 | 2-Furan-2-yl-6-(4-phenoxy-phenyl)-[1,2,4]triazolo[1,5-a]pyrazin-8-ylamine | 370 | Example 4 |
| Ex. 193 | 6-Dibenzofuran-4-yl-2-furan-2-yl-[1,2,4]triazolo[1,5-a]pyrazin-8-ylamine | 368 | Example 4 |
| Ex. 194 | 4-(8-Amino-2-furan-2-yl-[1,2,4]triazolo[1,5-a]pyrazin-6-yl)-benzonitrile | 303 | Example 4 |
| Ex. 195 | 6-(4-Amino-phenyl)-2-furan-2-yl-[1,2,4]triazolo[1,5-a]pyrazin-8-ylamine | 293 | Example 4 |
| Ex. 196 | 2-Furan-2-yl-6-phenoxathiin-4-yl-[1,2,4]triazolo[1,5-a]pyrazin-8-ylamine | 400 | Example 4 |
| Ex. 197 | 4-(8-Amino-2-furan-2-yl-[1,2,4]triazolo[1,5-a]pyrazin-6-yl)-benzoic acid | 322 | Example 4 |
| Ex. 198 | N-[3-(8-Amino-2-furan-2-yl-[1,2,4]triazolo[1,5-a]pyrazin-6-yl)-phenyl]-methanesulfonamide | 371 | Example 4 |

-continued

| Example | Name | MS (m/z) [M + H]+ | Synthetic Method |
|---|---|---|---|
| Ex. 199 | 2-Furan-2-yl-6-(3-methanesulfonyl-phenyl)-[1,2,4]triazolo[1,5-a]pyrazin-8-ylamine | 356 | Example 4 |
| Ex. 200 | 6-Benzo[1,3]dioxol-5-yl-2-furan-2-yl-[1,2,4]triazolo[1,5-a]pyrazin-8-ylamine | 322 | Example 4 |
| Ex. 201 | 2-Furan-2-yl-6-(6-methoxy-pyridin-3-yl)-[1,2,4]triazolo[1,5-a]pyrazin-8-ylamine | 309 | Example 4 |
| Ex. 202 | 2-Furan-2-yl-6-(3-methoxy-phenyl)-[1,2,4]triazolo[1,5-a]pyrazin-8-ylamine | 308 | Example 4 |
| Ex. 203 | N-[3-(8-Amino-2-furan-2-yl-[1,2,4]triazolo[1,5-a]pyrazin-6-yl)-phenyl]-acetamide | 335 | Example 4 |
| Ex. 204 | 1-[3-(8-Amino-2-furan-2-yl-[1,2,4]triazolo[1,5-a]pyrazin-6-yl)-phenyl]-ethanone | 320 | Example 4 |
| Ex. 205 | 6-(3,5-Dimethyl-isoxazol-4-yl)-2-furan-2-yl-[1,2,4]triazolo[1,5-a]pyrazin-8-ylamine | 297 | Example 4 |
| Ex. 206 | 2-Furan-2-yl-6-(3-trifluoromethyl-phenyl)-[1,2,4]triazolo[1,5-a]pyrazin-8-ylamine | 346 | Example 4 |
| Ex. 207 | 2-Furan-2-yl-6-pyrimidin-5-yl[1,2,4]triazolo[1,5-a]pyrazin-8-ylamine | 280 | Example 4 |
| Ex. 208 | 2-Furan-2-yl-6-(3-nitro-phenyl)-[1,2,4]triazolo[1,5-a]pyrazin-8-ylamine | 323 | Example 4 |
| Ex. 209 | 6-(3-Dimethylamino-phenyl)-2-furan-2-yl-[1,2,4]triazolo[1,5-a]pyrazin-8-ylamine | 321 | Example 4 |
| Ex. 210 | 4-(8-Amino-2-furan-2-yl-[1,2,4]triazolo[1,5-a]pyrazin-6-yl)-benzoic acid ethyl ester | 350 | Example 4 |
| Ex. 211 | 4-(8-Amino-2-furan-2-yl-[1,2,4]triazolo[1,5-a]pyrazin-6-yl)-benzoic acid methyl ester | 336 | Example 4 |
| Ex. 212 | 2-Furan-2-yl-6-(4-trifluoromethoxy-phenyl)-[1,2,4]triazolo[1,5-a]pyrazin-8-ylamine | 362 | Example 4 |
| Ex. 213 | 2-Furan-2-yl-6-(3-trifluoromethoxy-phenyl)-[1,2,4]triazolo[1,5-a]pyrazin-8-ylamine | 362 | Example 4 |
| Ex. 214 | 2-Furan-2-yl-6-(4-nitro-phenyl)-[1,2,4]triazolo[1,5-a]pyrazin-8-ylamine | 323 | Example 4 |
| Ex. 215 | 2-Furan-2-yl-6-(4-methanesulfonyl-phenyl)-[1,2,4]triazolo[1,5-a]pyrazin-8-ylamine | 356 | Example 4 |
| Ex. 216 | 3-(8-Amino-2-furan-2-yl-[1,2,4]triazolo[1,5-a]pyrazin-6-yl)-phenol | 294 | Example 4 |
| Ex. 217 | 4-(8-Amino-2-furan-2-yl-[1,2,4]triazolo[1,5-a]pyrazin-6-yl)-phenol | 294 | Example 4 |
| Ex. 218 | 4-(8-Amino-2-furan-2-yl-[1,2,4]triazolo[1,5-a]pyrazin-6-yl)-2-methoxy-phenol | 324 | Example 4 |
| Ex. 219 | 8-Amino-2-furan-2-yl-[1,2,4]triazolo[1,5-a]pyrazine-6-carboxylic acid butylamide | 301 | Example 11 |
| Ex. 220 | 8-Amino-2-furan-2-yl-[1,2,4]triazolo[1,5-a]pyrazine-6-carboxylic acid [2-(4-hydroxy-phenyl)-ethyl]-amide | 365 | Example 11 |
| Ex. 221 | 8-Amino-2-furan-2-yl-[1,2,4]triazolo[1,5-a]pyrazine-6-carboxylic acid (3-phenyl-propyl)-amide | 363 | Example 11 |
| Ex. 222 | 8-Amino-2-furan-2-yl-[1,2,4]triazolo[1,5-a]pyrazine-6-carboxylic acid benzylamide | 335 | Example 11 |
| Ex. 223 | 8-Amino-2-furan-2-yl-[1,2,4]triazolo[1,5-a]pyrazine-6-carboxylic acid benzyl-methyl-amide | 349 | Example 11 |
| Ex. 224 | (8-Amino-2-furan-2-yl-[1,2,4]triazolo[1,5-a]pyrazin-6-yl)-pyrrolidin-1-yl-methanone | 299 | Example 11 |
| Ex. 225 | (8-Amino-2-furan-2-yl-[1,2,4]triazolo[1,5-a]pyrazin-6-yl)-piperidin-1-yl-methanone | 313 | Example 11 |
| Ex. 226 | (8-Amino-2-furan-2-yl-[1,2,4]triazolo[1,5-a]pyrazin-6-yl)-morpholin-4-yl-methanone | 315 | Example 11 |
| Ex. 227 | 1-(8-Amino-2-furan-2-yl-[1,2,4]triazolo[1,5-a]pyrazine-6-carbonyl)-piperidine-3-carboxylic acid ethyl ester | 385 | Example 11 |
| Ex. 228 | (8-Amino-2-furan-2-yl-[1,2,4]triazolo[1,5-a]pyrazin-6-yl)-(4-benzyl-piperazin-1-yl)-methanone | 404 | Example 11 |
| Ex. 229 | (8-Amino-2-furan-2-yl-[1,2,4]triazolo[1,5-a]pyrazin-6-yl)-(4-pyridin-4-yl-piperazin-1-yl)-methanone | 391 | Example 11 |
| Ex. 230 | (8-Amino-2-furan-2-yl-[1,2,4]triazolo[1,5-a]pyrazin-6-yl)-(4-pyridin-2-yl-piperazin-1-yl)-methanone | 391 | Example 11 |

The $A_{2a}$ modulating activity, of compounds of the present invention can be assessed by methods described in the following examples.

EXAMPLE 231

Numerous compounds of the present invention were prepared (see working examples and table above) and tested. Specifically, the $K_i$ values for rat and human $A_1$ adenosine receptors and for human $A_{2a}$ adenosine receptors were determined according to the following binding assay protocol. The ratio $A_{2a}/A_1$ was also calculated.

Materials

Adenosine deaminase and HEPES were purchased from Sigma-Aldrich (St. Louis, Mo.). Ham's F-12 cell culture medium and fetal bovine serum were purchased from GIBCO Life Technologies (Gaithersburg, Md.). Antibiotic G-418, Falcon 150 mM culture plates and Costar 12-well culture plates were purchased from Fisher (Pittsburgh, Pa.). [$^3$H] CPX was purchased from DuPont-New England Nuclear Research Products (Boston, Mass.). Penicillin/streptomycin antibiotic mixture was purchased from Mediatech. (Washington, D.C.). The composition of HEPES-buffered Hank's solution was: 130 mM NaCl, 5.0 mM Cl, 1.5 mM CaCl$_2$, 0.41 mM MgS0$_4$, 0.49 mM Na$_2$HPO$_4$, 0.44 mM KH2PO$_4$, 5.6 mM dextrose, and 5 mM HEPES (pH 7.4).

Membrane Preparation

A$_{2a}$ Receptor: Membranes were prepared from rat brain tissues purchased from Pel-Freez. Tissues were homogenized in buffer A (10 mM EDTA, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 minutes. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Rat A$_1$ Receptor: Membranes were prepared from rat cerebral cortex isolated from freshly euthanized rats. Tissues were homogenized in buffer A (10 mM EDTA, 10 mM Na-HEPES, pH 7.4) supplemented with protease inhibitors (10 μg/ml benzamidine, 100 μM PMSF, and 2 μg/ml each of aprotinin, pepstatin and leupeptin), and centrifuged at 20,000×g for 20 minutes. Pellets were resuspended and washed twice with buffer HE (10 mM Na-HEPES, 1 mM EDTA, PH 7.4, pus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Radioligand Binding Assays

Membranes (40-70 μg membrane protein), radioligands and varying concentrations of test compounds of the present invention were incubated in triplicates in 0.1 ml buffer HE plus 2 units/ml adenosine deaminase for 2.5 hours at 21° C. Radioligand [$^3$H]DPCPX was used for competition binding assays on A$_1$ receptors and [$^3$H]ZM241385 as used for A$_{2a}$ adenosine receptors. Nonspecific binding was measured in the presence of 10 μM NECA for A$_1$ receptors, or 10 μM XAC for A$_{2a}$ receptors. Binding assays were terminated by filtration over Whatman GF/C glass fiber filters using a BRANDEL cell harvester. Filters were rinsed three times with 3-4 mL ice cold 10 mM Tris-HCl, pH 7.4 and 5 mM MgCl$_2$ at 4° C., and were counted in a Wallac β-counter.

Analysis of Binding Data

K$_i$ determination: Competition binding data were fit to a single-site binding model and plotted using Prizm GraphPad. Cheng-Prusoff equation $K_i=IC_{50}/(1+[I]/K_d)$ was used to calculate K$_i$ values from IC$_{50}$ values, where K$_i$ is the affinity constant for the competing test compound, [I] is the concentration of the free radioligand, and K$_d$ is the affinity constant for the radioligand.

A$_{2a}$ % binding: Data were generally expressed as percentage of total specific binding at 1 μM of competing test compound (% total specific binding)=100%×(specific binding with 1 μM of competing test compound/total specific binding).

Results

Compounds of the present invention typically exhibited K$_i$ values of less than 10 μM and A$_{2a}$ % binding ranging from 1% to 50%; some compounds exhibited K$_i$ values of less than 1 nM.

EXAMPLE 232

Catalepsy Experiments

Haloperidol-induced catalepsy was used to mimic the effects of Parkinson's disease in rats and mice. Animals were injected with haloperidol, which causes immobility: A test compound of the present invention was then administered orally and the compound's ability to reverse these Parkinson's-like symptoms was analyzed. For reference, see Sanberg et al., Behavioral Neuroscience 102: 748-759 (1988).

Rats

Male Sprague-Dawley rats (225-275 g) were injected with haloperidol (1 mg/kg s.c.) to induce catalepsy. These rats were then subjected to the bar test. In this test, the rats' forelimbs were placed on an aluminum bar (1 cm in diameter) suspended horizontally 10 cm above the surface of the bench. The elapsed time until the rat placed one forepaw back on the bench was measured, with a maximum time of 120 seconds allowed. It should be noted that these rats were in a cataleptic state and therefore were unable to correct an externally imposed posture (i.e., the cataleptic rats, when placed in this unnatural position, were unable to come down from the horizontal bar over a period of 120 seconds or more). Once the rats showed a stable baseline cataleptic response (about three hours after haloperidol injection), a test compound of the present invention or vehicle alone is administered orally, and catalepsy data from the bar test were measured every 30 minutes for the next 3 hours. Data were analyzed by one factor analysis of variance with Dunnett's 't' test used to make post-hoc comparisons. Many compounds of this invention showed oral activity at a dosage of 10 mg/kg or lower, which allowed the cataleptic animals to come down from the bar within 60 seconds and remained in a catalepsy-free state for at least 60 minutes.

Mice

Mice catalepsy experiment was conducted in the same manner as described above except mice (CD-1; 25-30 g) were used instead of rats, the dose of haloperidol was 3 mg/kg s.c. instead of 1 mg/kg s.c., and the bar was suspended 4.5 cm instead of 10 cm above the surface of the bench. Many compounds of this invention showed oral activity at a dosage of 10 mg/kg or lower, which allowed the cataleptic animals to come down from the bar within 60 seconds and remained in a catalepsy-free state for at least 60 minutes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the following formula:

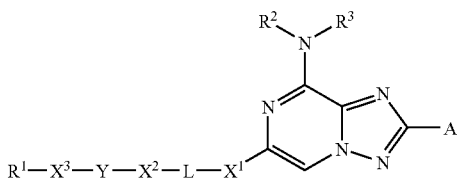

or a pharmaceutically acceptable salt or N-oxide thereof; wherein
A is aryl or furanyl;
$R^2$ and $R^3$ are hydrogen;
$X^1$ is alkynylene;
$X^2$, and $X^3$ are a bond;
L is a linker of the following formula:

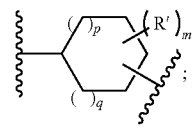

wherein:
R' is hydrogen, alkyl, alkenyl, alkynyl, alkoxy, acyl, halo, hydroxy, amino, nitro, oxo, thioxo, cyano, guanadino, amidino, carboxy, sulfo, sulfoxy, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl; provided that two adjacent R' groups can join together to form a 4- to 8-membered optionally substituted cyclic moiety;

each of p, q, and m, independently, is 0-3;
Y is a bond; and
$R^1$ is hydrogen.

2. A pharmaceutical composition comprising a compound of claim 1 and a pharmaceutically acceptable carrier.

3. The following compound:
2-Furan-2-yl-6-[1-(2,4,6-trifluoro-benzylamino)-cyclohexylethynyl]-[1,2,4]triazolo[1,5-a]pyrazin-8-ylamine.

4. The following compound:
1-(8-Amino-2-furan-2-yl-[1,2,4]triazolo [1,5-a]pyrazin-6-ylethynyl)-cyclobutanol.

5. The following compound:
1-(8-Amino-2-furan-2-yl- [1,2,4]triazolo [1,5-a]pyrazin-6-ylethynyl)-cyclopentanol.

6. The following compound:
1- [8-Amino-2-(3-fluoro-phenyl)- [1,2,4]triazolo[1,5-a]pyrazin-6-ylethynyl]-cyclopentanol.

7. The following compound:
1-(8-Amino-2-furan-2-yl- [1,2,4]triazolo [1,5-a]pyrazin-6-ylethynyl)-cyclohexanol.

8. The following compound:
2-(8-Amino-2-furan-2-yl- [1,2,4]triazolo[1,5-a]pyrazin-6-ylethynyl)-indan-2-ol.

9. The following compound:
1-(8-Amino-2-furan-2-yl- [1,2,4]triazolo [1,5-a]pyrazin-6-ylethynyl)-2,2,6-trimethyl-cyclohexanol.

10. The following compound:
6-(3-Cyclohexyl-prop- 1-ynyl)-2-furan-2-yl- [1,2,4]triazolo[1,5-a]pyrazin-8-ylamine.

11. The following compound:
6-(3-Cyclopentyl-prop- 1-ynyl)-2-furan-2-yl- [1,2,4]triazolo[1,5-a]pyrazin-8-ylamine.

12. The following compound:
6-(1-Amino-cyclohexylethynyl)-2-furan-2-yl- [1,2,4]triazolo[1,5-a]pyrazin-8-ylamine.

13. A pharmaceutical composition comprising a compound of anyone of claims 3-12 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,674,791 B2 | Page 1 of 1 |
| APPLICATION NO. | : 10/552305 | |
| DATED | : March 9, 2010 | |
| INVENTOR(S) | : James E. Dowling et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 862 days.

Signed and Sealed this

Fourth Day of January, 2011

David J. Kappos
*Director of the United States Patent and Trademark Office*